(12) United States Patent
Goldman et al.

(10) Patent No.: US 7,396,355 B2
(45) Date of Patent: *Jul. 8, 2008

(54) METHOD AND APPARATUS FOR APPLYING ENERGY TO BIOLOGICAL TISSUE INCLUDING THE USE OF TUMESCENT TISSUE COMPRESSION

(75) Inventors: Mitchel P. Goldman, La Jolla, CA (US); Robert A. Weiss, Baltimore, MD (US); Arthur W. Zikorus, San Jose, CA (US); James G. Chandler, Boulder, CO (US)

(73) Assignee: VNUS Medical Technologies, Inc., Sunnyvale, CA (US)

( * ) Notice: Subject to any disclaimer, the term of this patent is extended or adjusted under 35 U.S.C. 154(b) by 434 days.

This patent is subject to a terminal disclaimer.

(21) Appl. No.: 10/872,646

(22) Filed: Jun. 21, 2004

(65) Prior Publication Data

US 2004/0243201 A1 Dec. 2, 2004

Related U.S. Application Data

(63) Continuation of application No. 09/899,885, filed on Jul. 6, 2001, now Pat. No. 6,752,803, which is a continuation of application No. 09/267,127, filed on Mar. 10, 1999, now Pat. No. 6,258,084, which is a continuation-in-part of application No. 09/138,472, filed on Aug. 21, 1998, now Pat. No. 6,179,832, which is a continuation-in-part of application No. 08/927,251, filed on Sep. 11, 1997, now Pat. No. 6,200,312.

(51) Int. Cl.
*A61B 18/18* (2006.01)

(52) U.S. Cl. ............... 606/41; 128/898; 607/105

(58) Field of Classification Search ............ 606/27–29, 606/31–32, 34, 41, 42; 607/96, 98, 100–102, 607/104–106

See application file for complete search history.

(56) References Cited

U.S. PATENT DOCUMENTS 3,301,258 A 1/1967 Werner et al.
4,564,011 A 1/1986 Goldman
4,643,186 A 2/1987 Rosen et al.
4,660,571 A 4/1987 Hess et al.
4,776,349 A 10/1988 Nashef et al.

(Continued)

FOREIGN PATENT DOCUMENTS

EP 0 189 329 A2 7/1986

(Continued)

OTHER PUBLICATIONS

Min et al, U.S. Appl. No. 60/118,050, filed Feb. 1, 1999.

(Continued)

*Primary Examiner*—Michael Peffley
(74) *Attorney, Agent, or Firm*—Knobbe, Martens, Olson & Bear LLP

(57) ABSTRACT

An electrode catheter is introduced into a hollow anatomical structure, such as a vein, and is positioned at a treatment site within the structure. Tumescent fluid is injected into the tissue surrounding the treatment site to produce tumescence of the surrounding tissue which then compresses the vein. The solution may include an anesthetic, and may further include a vasoconstrictive drug that shrinks blood vessels. The tumescent swelling in the surrounding tissue causes the hollow anatomical structure to become compressed, thereby exsanguinating the treatment site. Energy is applied by an electrode catheter in apposition with the vein wall to create a heating effect. The heating effect causes the hollow anatomical structure to become molded and durably assume the compressed dimensions caused by the tumescent technique. The electrode catheter can be moved within the structure so as to apply energy to a large section of the hollow anatomic structure. In a further aspect, the location of the electrodes is determined by impedance monitoring. Also, temperature sensors at the treatment site are averaged to determine the site temperature.

25 Claims, 6 Drawing Sheets

U.S. PATENT DOCUMENTS

| | | | |
|---|---|---|---|
| 5,122,137 A | 6/1992 | Lennox | |
| 5,127,902 A | 7/1992 | Fischell | |
| 5,188,602 A | 2/1993 | Nichols | |
| 5,556,396 A | 9/1996 | Cohen et al. | |
| 5,695,495 A | 12/1997 | Ellman et al. | |
| 5,709,224 A | 1/1998 | Behl et al. | |
| 5,827,268 A | 10/1998 | Laufer | |
| 5,863,290 A | 1/1999 | Gough et al. | |
| 6,033,397 A | 3/2000 | Laufer et al. | |
| 6,033,398 A | 3/2000 | Farley et al. | |
| 6,036,687 A | 3/2000 | Laufer et al. | |
| 6,139,527 A | 10/2000 | Laufer et al. | |
| 6,152,899 A | 11/2000 | Farley et al. | |
| 6,210,402 B1 | 4/2001 | Olsen et al. | |
| 6,228,082 B1 * | 5/2001 | Baker et al. | 606/49 |
| 6,258,084 B1 | 7/2001 | Goldman et al. | |
| 6,398,777 B1 | 6/2002 | Navarro et al. | |
| 6,401,719 B1 * | 6/2002 | Farley et al. | 128/898 |
| 6,689,126 B1 | 2/2004 | Farley et al. | |
| 6,752,803 B2 * | 6/2004 | Goldman et al. | 606/32 |

FOREIGN PATENT DOCUMENTS

| | | |
|---|---|---|
| EP | 0 727 184 A1 | 8/1996 |
| SU | 207289 | 12/1967 |
| WO | WO 93/21846 | 11/1993 |
| WO | WO 94/07446 | 4/1994 |
| WO | WO 95/31142 | 11/1995 |
| WO | WO 97/32532 | 9/1997 |
| WO | WO 98/19613 | 5/1998 |

OTHER PUBLICATIONS

Min et al, U.S. Appl No. 60/119,235, filed Feb. 9, 1999.

Excerpt from file history of US 6,769,433: preliminary amendment of Sep. 2001, office action of Sep. 2002, amendment of Mar. 2003, office action of Jul. 2003, amendments of Dec. 2003 and Jan. 2004, notice of allowability of Apr. 2004.

Excerpt from file history of US 6,237,606: original claims, preliminary amendement of Mar. 1999, office action of Feb. 2000, amendment of Apr. 2000, office action of Jul. 2000, summary of interview of Sep. 2000, amendment of Oct. 2000, notice of allowability of Jan. 2001.

Excerpt from file history of U.S. Appl. No. 10/900,563: original claims, office action of Jan. 2005, amendment of Apr. 2005, office action of Jun. 2005, office action of Dec. 2005, amendment of May 2006, office action of Aug. 2006, summary of interview of Jan. 2007, office action response of Jan. 2007, office action of Apr. 2007, response filed Jul. 2007, supplemental response filed Aug. 2007.

Excerpt from file history of US 6,752,803: preliminary amendment of Jul. 2001, office action of Sep. 2002, amendment of Mar. 2003, office action of Jun. 2003, summary of interview of Oct. 2003, amendment of Oct. 2003, office action of Nov. 2003, response of Jan. 2004, notice of allowability of Feb. 2004.

Excerpt from file history of US 6,258,084: original claims, office action of Apr. 2000, amendment of Aug. 2000, summary of interview of Dec. 2000, notice of allowability of Dec. 2000.

Excerpt from file history of U.S. Appl. No. 10/738,488: preliminary amendment of Mar. 2004, office action of Mar. 2006, response of Apr. 2006, office action of Jun. 2006, summary of interview of Oct. 2006, amendment of Oct. 2006, office action of Jun. 2007, summary of interview of Aug. 2007, amendment filed Sep. 2007.

Excerpt from file history of US 6,682,526: original claims, preliminary amendments of Nov. 2000, Jan. 2001, May 2001, office action of Feb. 2002, response of Mar. 2002, office action of Jul. 2002, amendment of Jan. 2003, office action of Mar. 2003, amendment of Aug. 2003, notice of allowability of Sep. 2003.

Excerpt from file history of U.S. Appl. No. 10/164,928: original claims, office action of Oct. 2003, amendment of Apr. 2004, office action of Jul. 2004, terminal disclaimer of Aug. 2004, restriction requirement of Jul. 2007, amendment and response filed Oct. 2007.

Excerpt from file history of US 6,401,719: original claims, office action of Oct. 2000, amendment of Dec. 2000, office action of Mar. 2001, amendment of Jul. 2001, office action of Aug. 2001, response of Nov. 2001, notice of allowability of Mar. 2002.

Ogawa et al., Electrothrombosis as a Treatment of Cirsoid Angioma in the Face and Scalp and Varicosis of the Leg, Plastic & Reconstructive Surgery, vol. 70, No. 3, pp. 310-318, Sep. 1982.

Partsch, Compression Therapy of the Legs, J. Dermatol. Surg. Oncol. 17:799-805, 1991.

*VNUS Medical Technologies v. Diomed Holdings et al* (N.D. Cal., Case No. C05-02972 MMC): Defendants' Joint Motion and Brief in Support of Motion for Summary Judgment of Invalidity Under 35 USC §§ 102-103 (unredacted version), dated Aug. 10, 2007.

*VNUS Medical Technologies v. Diomed Holdings et al* (N.D. Cal., Case No. C05-02972 MMC): Declaration of Charles T. Steenburg (with Exhibits I, O-Q, BB and DD thereto) in support of Defendants' Joint Motion for Summary Judgment of Invalidity Under 35 USC §§ 102-103, dated Aug. 10, 2007.

*VNUS Medical Technologies v. Diomed Holdings et al* (N.D. Cal., Case No. C05-02972 MMC): Defendants' Joint Reply Brief in Support of Motion for Summary Judgment of Invalidity Under 35 USC §§ 102-103 (unredacted version), dated Aug. 31, 2007.

*VNUS Medical Technologies v. Diomed Holdings et al* (N.D. Cal., Case No. C05-02972 MMC): Declaration of Charles T. Steenburg (with Exhibits KK, MM and OO thereto) in support of Defendants' Joint Reply Brief in Support of Motion for Summary Judgment of Invalidity Under 35 USC §§ 102-103, dated Aug. 31, 2007.

*VNUS Medical Technologies v. Diomed Holdings et al* (N.D. Cal., Case No. C05-02972 MMC): Defendants' Joint Motion and Brief in Support of Motion for Summary Judgment of Invalidity Under 35 USC § 112 (unredacted version), dated Aug. 10, 2007.

*VNUS Medical Technologies v. Diomed Holdings et al* (N.D. Cal., Case No. C05-02972 MMC): Declaration of Dr. R. Rox Anderson in support of Defendants' Joint Motion for Summary Judgment of Invalidity Under 35 USC § 112, dated Aug. 10, 2007.

*VNUS Medical Technologies v. Diomed Holdings et al* (N.D. Cal., Case No. C05-02972 MMC): Declaration of Richard J. Twilley (with Exhibits C, I, L-N and R-U thereto) in support of Defendants' Joint Motion for Summary Judgment of Invalidity Under 35 USC § 112, dated Aug. 10, 2007.

*VNUS Medical Technologies v. Diomed Holdings et al* (N.D. Cal., Case No. C05-02972 MMC): Defendants' Joint Reply Brief in Support of Motion for Summary Judgment of Invalidity Under 35 USC § 112 (unredacted version), dated Aug. 31, 2007.

*VNUS Medical Technologies v. Diomed Holdings et al* (N.D. Cal., Case No. C05-02972 MMC): Declaration of Eric E. Grondahl (with Exhibits A-D thereto) in support of Defendants' Joint Reply Brief in Support of Motion for Summary Judgment of Invalidity Under 35 USC § 112, dated Aug. 31, 2007.
*VNUS Medical Technologies v. Diomed Holdings et al* (N.D. Cal., Case No. C05-02972 MMC): Defendant Diomed's Answer to First Amended Complaint, dated Oct. 31, 2005.
*VNUS Medical Technologies v. Diomed Holdings et al* (N.D. Cal., Case No. C05-02972 MMC): Plaintiff VNUS's Answer to Counterclaims of Diomed Asserted in Response to First Amended Complaint, dated Nov. 23, 2005.
*VNUS Medical Technologies v. Diomed Holdings et al* (N.D. Cal., Case No. C05-02972 MMC): Plaintiff's Disclosure of Asserted Claims and Preliminary Infringement Contentions, dated Jan. 23, 2006, and Exhibits A-C thereto.
*VNUS Medical Technologies v. Diomed Holdings et al* (N.D. Cal., Case No. C05-02972 MMC): Diomed Holdings, Inc. and Diomed, Inc.'s Preliminary Invalidity Contentions Pursuant to Patent Local Rule 3-3, dated Mar. 9, 2006, and Exhibits A-D thereto.
*VNUS Medical Technologies v. Diomed Holdings et al* (N.D. Cal., Case No. C05-02972 MMC): Supplemental Submission by Diomed Holdings, Inc. and Diomed, Inc. Regarding Their Preliminary Invalidity Contentions, dated Apr. 11, 2006.
*VNUS Medical Technologies v. Diomed Holdings et al* (N.D. Cal., Case No. C05-02972 MMC): Vascular Solutions, Inc.'s Disclosure of Preliminary Invalidity Contentions, dated Mar. 9, 2006, and Exhibits A-D thereto.
*VNUS Medical Technologies v. Diomed Holdings et al* (N.D. Cal., Case No. C05-02972 MMC): Angiodynamics, Inc.'s Disclosure of Preliminary Invalidity Contentions, dated Mar. 9, 2006, and Exhibits A-E thereto.
*VNUS Medical Technologies v. Diomed Holdings et al* (N.D. Cal., Case No. C05-02972 MMC): Plaintiff's Disclosure of Asserted Claims and Final Infringement Contentions, dated Dec. 20, 2006, and Exhibits A-C thereto.
*VNUS Medical Technologies v. Diomed Holdings et al* (N.D. Cal., Case No. C05-02972 MMC): Diomed Holdings, Inc. and Diomed, Inc.'s Final Invalidity Contentions Pursuant to Patent Local Rule 3-6, dated Jan. 9, 2007.
*VNUS Medical Technologies v. Diomed Holdings et al* (N.D. Cal., Case No. C05-02972 MMC): Angiodynamics, Inc.'s Disclosure of Final Invalidity Contentions, dated Jan. 9, 2007, and Exhibit C thereto.
*VNUS Medical Technologies v. Diomed Holdings et al* (N.D. Cal., Case No. C05-02972 MMC): Vascular Solutions, Inc.'s Final Invalidity Contentions, dated Jan. 9, 2007, and Exhibit C thereto.
*VNUS Medical Technologies v. Diomed Holdings et al* (N.D. Cal., Case No. C05-02972 MMC): VNUS Medical Technologies' Opening Claim Construction Brief dated Aug. 22, 2006, Appendix 1 and 2 thereto and Proposed Claim Construction Order.
*VNUS Medical Technologies v. Diomed Holdings et al* (N.D. Cal., Case No. C05-02972 MMC): Defendants' Joint Claim Construction Brief dated Sep. 19, 2006, and accompanying Proposed Claim Construction Order, Declaration of Mark N. Isaacs, M.D. in Support of Defendants' Claim Construction Brief, and Declaration of Ted R. Kohler, M.D. in Support of Defendants' Claim Construction Brief.
*VNUS Medical Technologies v. Diomed Holdings et al* (N.D. Cal., Case No. C05-02972 MMC): Individual Claim Construction Brief of Diomed Holdings Inc. and Diomed, Inc. dated Sep. 19, 2006, and accompanying Proposed Claim Construction Order.

*VNUS Medical Technologies v. Diomed Holdings et al* (N.D. Cal., Case No. C05-02972 MMC): Angiodynamics, Inc.'s Claim Construction Brief dated Sep. 19, 2006.
*VNUS Medical Technologies v. Diomed Holdings et al* (N.D. Cal., Case No. C05-02972 MMC): Vascular Solutions, Inc.'s Claim Construction Brief dated Sep. 19, 2006, Appendix 1 thereto and accompanying Proposed Claim Construction Order.
*VNUS Medical Technologies v. Diomed Holdings et al* (N.D. Cal., Case No. C05-02972 MMC): VNUS Medical Technologies, Inc.'s Reply Claim Construction Brief, dated Oct. 11, 2006.
*VNUS Medical Technologies v. Diomed Holdings et al* (N.D. Cal., Case No. C05-02972 MMC): Amended Patent Rule 4-3b Chart, dated Oct. 23, 2006.
*VNUS Medical Technologies v. Diomed Holdings et al* (N.D. Cal., Case No. C05-02972 MMC): Amended Order Construing Claims, dated Nov. 22, 2006.
*VNUS Medical Technologies v. Diomed Holdings et al* (N.D. Cal., Case No. C05-02972 MMC): Diomed Holdings, Inc. and Diomed, Inc's Response to VNUS Medical Technologies' Third Set of Interrogatories, dated Apr. 18, 2007, and Exhibits A-B thereto.
*VNUS Medical Technologies v. Diomed Holdings et al* (N.D. Cal., Case No. C05-02972 MMC): Plaintiff VNUS's Motion and Brief in Support of Motion for Summary Judgment on Patent Infringement (redacted version), refiled and dated Aug. 28, 2007, and Declaration of Howard Greisler M.D. in support thereof (redacted version).
*VNUS Medical Technologies v. Diomed Holdings et al* (N.D. Cal., Case No. C05-02972 MMC): Defendant Diomed's Opposition to VNUS's Motion for Summary Judgment on Patent Infringement (redacted version), refiled and dated Sep. 12, 2007.
*VNUS Medical Technologies v. Diomed Holdings et al* (N.D. Cal., Case No. C05-02972 MMC): Defendants Angiodynamics' and VSI's Joint Opposition to VNUS's Motion for Summary Judgment on Patent Infringement (redacted version), refiled and dated Sep. 12, 2007.
*VNUS Medical Technologies v. Diomed Holdings et al* (N.D. Cal., Case No. C05-02972 MMC): Plaintiff VNUS's Reply Brief in Support of Motion for Summary Judgment on Patent Infringement, dated Aug. 31, 2007.
*VNUS Medical Technologies v. Diomed Holdings et al* (N.D. Cal., Case No. C05-02972 MMC): Defendants' Joint Motion and Brief in Support of Motion for Summary Judgment of Invalidity Under 35 USC §§ 102-103 (redacted version), dated Aug. 10, 2007.
*VNUS Medical Technologies v. Diomed Holdings et al* (N.D. Cal., Case No. C05-02972 MMC): Declaration of Dr. J. Kevin McGraw (with Appendices A&B thereto) in support of Defendants' Joint Motion and Brief in Support of Motion for Summary Judgment of Invalidity Under 35 USC §§ 102-103, dated Aug. 10, 2007.
*VNUS Medical Technologies v. Diomed Holdings et al* (N.D. Cal., Case No. C05-02972 MMC): Declaration of Charles T. Steenburg (with Exhibits A, D, K-N, R, T-Z, AA, CC, EE, FF and HH thereto) in support of Defendants' Joint Motion for Summary Judgment of Invalidity Under 35 USC §§ 102-103, dated Aug. 10, 2007.
*VNUS Medical Technologies v. Diomed Holdings et al* (N.D. Cal., Case No. C05-02972 MMC): Plaintiff VNUS' Opposition to Motion for Summary Judgment of Invalidity Under 35 USC §§ 102-103 (redacted version), dated Aug. 24, 2007, and Declaration of Dr. Mitchel P. Goldman (with Appendices A-D thereto) in support thereof.
*VNUS Medical Technologies v. Diomed Holdings et al* (N.D. Cal., Case No. C05-02972 MMC): Defendants' Joint Reply Brief in Support of Motion for Summary Judgment of Invalidity Under 35 USC §§ 102-103 (redacted version), dated Aug. 31, 2007.
*VNUS Medical Technologies v. Diomed Holdings et al* (N.D. Cal., Case No. C05-02972 MMC): Declaration of Charles T. Steenburg (with Exhibits II, LL, and NN thereto) in support of Defendants' Joint Reply Brief in Support of Motion for Summary Judgment of Invalidity Under 35 USC §§ 102-103, dated Aug. 31, 2007.
*VNUS Medical Technologies v. Diomed Holdings et al* (N.D. Cal., Case No. C05-02972 MMC): Plaintiff VNUS' Supplemental Opposition to Motion for Summary Judgment of Invalidity Under 35 USC §§ 102-103 and Exhibit A thereto (redacted version), dated Oct. 10, 2007, and Declaration of Dr. Mitchel P. Goldman in support thereof.
*VNUS Medical Technologies v. Diomed Holdings et al* (N.D. Cal., Case No. C05-02972 MMC): Defendants' Joint Motion and Brief in Support of Motion for Summary Judgment of Invalidity Under 35 USC § 112 (redacted version), dated Aug. 10, 2007.
*VNUS Medical Technologies v. Diomed Holdings et al* (N.D. Cal., Case No. C05-02972 MMC): Declaration of Richard J. Twilley (with Exhibits A, D, F-H, K, O, Q, and V thereto) in support of Defendants' Joint Motion for Summary Judgment of Invalidity Under 35 USC §112, dated Aug. 10, 2007.
*VNUS Medical Technologies v. Diomed Holdings et al* (N.D. Cal., Case No. C05-02972 MMC): Plaintiff VNUS' Opposition to Motion for Summary Judgment of Invalidity Under 35 USC §112 (redacted version), dated Aug. 24, 2007.
*VNUS Medical Technologies v. Diomed Holdings et al* (N.D. Cal., Case No. C05-02972 MMC): Defendants' Joint Reply Brief in Support of Motion for Summary Judgment of Invalidity Under 35 USC § 112 (redacted version), dated Aug. 31, 2007.
*VNUS Medical Technologies v. Diomed Holdings et al* (N.D. Cal., Case No. C05-02972 MMC): Declaration of Eric E. Grondahl (without Exhibits) in support of Defendants' Joint Reply Brief in Support of Motion for Summary Judgment of Invalidity Under 35 USC § 112, dated Aug. 31, 2007.
*VNUS Medical Technologies v. Diomed Holdings et al* (N.D. Cal., Case No. C05-02972 MMC): Order Denying Plaintiff VNUS's Motion for Summary Judgment on Patent Infringement; Denying Defendants' Motion for Summary Judgment on Enablement and Written Description; and Denying in Part and Deferring in Part Ruling on Defendants' Motion for Summary Judgment Under 35 USC §§ 102-103; dated Oct. 2, 2007.
*VNUS Medical Technologies v. Diomed Holdings et al* (N.D. Cal., Case No. C05-02972 MMC): Order Denying Deferred Portion of Defendants' Motion for Summary Judgment Under 35 USC §§ 102-103, dated Oct. 22, 2007.
*VNUS Medical Technologies v. Diomed Holdings et al* (N.D. Cal., Case No. C05-02972 MMC): Defendants' Joint Motion in Limine#1 and Brief in support thereof, dated Oct. 1, 2007.
*VNUS Medical Technologies v. Diomed Holdings et al* (N.D. Cal., Case No. C05-02972 MMC): Plaintiff VNUS' Opposition to Defendants' Motion in Limine #1, dated Oct. 9, 2007.
*VNUS Medical Technologies v. Diomed Holdings et al* (N.D. Cal., Case No. C05-02972 MMC): Order Granting Defendants' Joint Motion in Limine #1, dated Oct. 22, 2007.
*VNUS Medical Technologies v. Diomed Holdings et al* (N.D. Cal., Case No. C05-02972 MMC): Plaintiff VNUS' Motion in Limine and Brief in Support Thereof, to Exclude the Thesis of Dr. Bone-Salat, Evidence of Inventive Activity in Spain, and Uncorroborated Communications About Such Activity, dated Oct. 1, 2007.
*VNUS Medical Technologies v. Diomed Holdings et al* (N.D. Cal., Case No. C05-02972 MMC): Defendants' Joint Opposition to Motion in Limine to Exclude the Thesis of Dr. Bone-Salat, Evidence of Inventive Activity in Spain, and Uncorroborated Communications About Such Activity (redacted version), dated Oct. 16, 2007, and Declarations of Dr. Carlos Bone-Salat in support thereof.
*VNUS Medical Technologies v. Diomed Holdings et al* (N.D. Cal., Case No. C05-02972 MMC): Plaintiff VNUS' Motion in Limine and Brief in Support Thereof, to Exclude Expert Trial Testimony of Drs. R. Rox Anderson, Irving J. Bigio, J. Kevin McGraw and Cynthia K. Shortell, dated Oct. 1, 2007.
*VNUS Medical Technologies v. Diomed Holdings et al* (N.D. Cal., Case No. C05-02972 MMC): Defendants' Joint Opposition to Motion in Limine to Exclude Expert Trial Testimony of Drs. R. Rox Anderson, Irving J. Bigio, J. Kevin McGraw and Cynthia K. Shortell, dated Oct. 16, 2007.
*VNUS Medical Technologies v. Diomed Holdings et al* (N.D. Cal., Case No. C05-02972 MMC): Expert Report of Robert A. Weiss, M.D. (with Exhibits A, C and D thereto), dated May 25, 2007.
*VNUS Medical Technologies v. Diomed Holdings et al* (N.D. Cal., Case No. C05-02972 MMC): Expert Report of Howard P. Greisler, M.D., dated May 25, 2007.
*VNUS Medical Technologies v. Diomed Holdings et al* (N.D. Cal., Case No. C05-02972 MMC): Expert Report of R. Rox Anderson, M.D., dated May 25, 2007.
*VNUS Medical Technologies v. Diomed Holdings et al* (N.D. Cal., Case No. C05-02972 MMC): Expert Report of Irving J. Bigio, Ph.D. (with Exhibit B thereto), dated May 25, 2007.
*VNUS Medical Technologies v. Diomed Holdings et al* (N.D. Cal., Case No. C05-02972 MMC): Expert Report of Dr. J. Kevin McGraw (with Appendices B-D thereto), dated May 25, 2007.
*VNUS Medical Technologies v. Diomed Holdings et al* (N.D. Cal., Case No. C05-02972 MMC): Expert Report of Eugene C. Rzucidlo, Esq. (with Appendix C thereto), dated May 25, 2007.
*VNUS Medical Technologies v. Diomed Holdings et al* (N.D. Cal., Case No. C05-02972 MMC): Expert Report of Russell H. Samson, M.D. (with Exhibits C-F thereto), dated May 25, 2007.
*VNUS Medical Technologies v. Diomed Holdings et al* (N.D. Cal., Case No. C05-02972 MMC): Expert Report of Cynthia K. Shortell, M.D., dated May 25, 2007.
*VNUS Medical Technologies v. Diomed Holdings et al* (N.D. Cal., Case No. C05-02972 MMC): Expert Report of Warren Grundfest, M.D. (with Appendix A thereto), dated Jun. 15, 2007.
*VNUS Medical Technologies v. Diomed Holdings et al* (N.D. Cal., Case No. C05-02972 MMC): Rebuttal Expert Report of Robert A. Weiss, M.D. (with Exhibits A-B thereto), dated Jun. 15, 2007.
*VNUS Medical Technologies v. Diomed Holdings et al* (N.D. Cal., Case No. C05-02972 MMC): Rebuttal Expert Report of Charles E. Van Horn, Esq. (with Exhibits D-F thereto), dated Jun. 15, 2007.

*VNUS Medical Technologies v. Diomed Holdings et al* (N.D. Cal., Case No. C05-02972 MMC): Rebuttal Expert Report of R. Rox Anderson, M.D., dated Jun. 15, 2007.

*VNUS Medical Technologies v. Diomed Holdings et al* (N.D. Cal., Case No. C05-02972 MMC): Rebuttal Expert Report of Dr. J. Kevin McGraw (redacted), dated Jun. 15, 2007.

*VNUS Medical Technologies v. Diomed Holdings et al* (N.D. Cal., Case No. C05-02972 MMC): Rebuttal Expert Report of Russell H. Samson, M.D., dated Jun. 15, 2007.

Muranov, A.N., "Electrocoagulation Treatment of Varicose Veins of the Lower Extremities," Medical Lit. State Pub., vol. 88, May 5, 1962.

Milostanov, V.N., "Electrocoagulation as the Method of Choice for Surgical Treatment of Varicose Veins of the Lower Extremities," State Medical Publishers of the Ukrainian SSR, Mar. 1962.

Milostanov, V.N., "Endovascular Electrocoagulation: The Operation of Choice in Treating Varicose Veins of the Lower Extremities," Saratov, Sep. 12-15, 1966.

Lamper, S.R., "Pathologic-Morphological Changes in the Veins after Endovascular Electrocoagulation," Stavropol, 1967.

Hejhal, et al., "Endovascular Electrocoagulation of Superficial Varices of the Lower Limbs," Rozhledy v Chirurgi 38, Jun. 1959, pp. 418-425.

Lamper, "Electrocoagulation Method to Treat Varicose Veins of the Lower Extremity," Khirurgia (Mosk.) 40, Nov. 1964, pp. 111-116.

Money, "Endovascular Electroablation of Peripheral Veins," 22nd Annual Symposium, Current Critical Problems, New Horizons and Techniques in Vascular and Endovascular Surgery, Nov. 1995.

O'Reilly, "Endovenous Diathermy Sclerosis of Varicose Veins," The Australian, New Zealand Journal of Surgery, vol. 47, No. 3, Jun. 1977, pp. 393-395.

Politowski, et al., "Complications and Difficulties in Electrocoagulation of Varices of the Lower Extremities," Surgery, Jun. 1966, vol. 59, No. 6, pp. 932-934.

Crockett, et al., "Preliminary Experience With An Endovascular Catheter for Electrocoagulation of Peripheral Veins," The Journal of Vascular Technology, Winter 1996, pp. 19-22.

O'Reilly, "Endovenous Diathermy Sclerosis as a Unit of the Armamentarium for the Attack on Varicose Veins," The Medical Journal of Australia, Jun. 1, 1974, p. 900.

Ershov & Safonov, "Multimodality Treatment of Varicosity With Electrocoagulation Medical Guidelines," May 5, 1974, Moscow.

Becker, et al., "Long-Term Occlusion of the Porcine Cystic Duct by Means of Endoluminal Radio-Frequency Electrocoagulation," Radiology, Apr. 1988, pp. 63-68.

Cragg, et al., "Endovascular Diathermic Vessel Occlusion," Diagnostic Radiology 144: pp. 303-308, Jul. 1982.

Frantsev, et al., "Treatment of Varicose Disease," Sov Med 1991, 1:22-25.

Ershov, "Treatment of Varicose Veins of the Lower Limbs," 1968, USSR Academy of Medical Science, pp. 1-15.

Frantsev, et al., "New Electrodes for Electrosurgical Treatment of Subcutaneous Varicose Veins," May 1973, 110(5), pp. 115-117.

Sokolnicki, et al., "Attempts to Coagulate Varices of the Lower Limbs with High-Frequency Current," Polish Medical Weekly, Jul. 1966, No. 27, pp. 1024-1026.

Frantsev, "Use of Puncture Monoactive Electrodes in the Treatment of Varicose Veins of the Lower Limbs," Nov. 1970, 105(11):77-80.

Gardner, et al., "Treatment of Arteriovenous Malformation by Endarterial Electrocoagulation," Brit. J. Surg., Feb. 1972, vol. 59, No. 2, pp. 146-148.

Thompson, et al., "Transcatheter Electrocoagulation: A Therapeutic Angiographic Technique for Vessel Occlusion," Investigative Radiology, Mar.-Apr. 1977, vol. 12, No. 2, pp. 146-153.

Thompson, et al., "Transcatheter Electrocoagulation: Experimental Evaluation of the Anode," Investigative Radiology, Jan.-Feb. 1979, vol. 14, pp. 41-47.

Thompson, et al., "Vessel Occlusion with Transcatheter Electrocoagulation: Initial Clinical Experience," Diagnostic Radiology, Nov. 1979, vol. 133, pp. 335-340.

Ziada, "Electro-Diathermy of the Long Saphenous Vein in Situ as an Alternative to Stripping," J. Egypt Med. Assoc., 1977, vol. 60, pp. 821-822.

Becker, et al., "Catheter for Endoluminal Bipolar Electrocoagulation," Radiology, Feb. 1989, vol. 170, No. 2, pp. 561-562.

Aaron, M.D., et al., "The Medical Letter on Drugs and Therapeutics," Drug and Therapeutic Information Inc., Jul. 12, 1968, pp. 53-55.

Gradman, "Venoscopic Obliteration of Variceal Tributaries Using Monopolar Electrocautery," Journal of Dermatology Surgery Oncology, 1994, 20, pp. 482-485.

Musaev, S.M., "Intravascular Electrocoagulation of Dilated Subcutaneous Varicose Veins of the Lower Extremities," Eksp Khir Anesteziol. Jul.-Aug. 1963, 27:36-7.

Phillips, et al., "Videoscopic Subfascial Incompetent Perforator Vein Ablation," British Journal of Surgery, 1996, 83, p. 1552.

Ralston, et al., "Effect of Increasing Current and Decreasing Blood Flow for Transcatheter Electrocoagulation," Investigative Radiology, Mar.-Apr. 1982, vol. 17, pp. 171-177.

Watts, "Endovenous Diathermy Destruction of Internal Saphenous," British Medical Journal, Oct. 7, 1972, p. 53.

Ward, "The Treatment of Orbital Varicosities," Arch Otolaryngol Head Neck Surg, Mar. 1987, vol. 113, pp. 286-288.

Politowski, "Treatment of Varicose Veins of the Lower Limbs with the Aid of Electrocoagulation," Pol Przegl Chir. Jan. 1964; 36:7-14.

Goldman, et al., "Diagnosis and Treatment of Varicose Veins: A Review," Journal of the American Academy of Dermatology, Sep. 1994, vol. 31, No. 3, pp. 393-413.

Ruju, et al., "Stripping of the Internal Saphenous Vein by "Tumescent Technique" and Under Local Anesthesia," G Ital. Chir. Vasc. 1998: pp. 43-46.

Nabatoff, "A Complete Stripping of Varicose Veins Under Local Anesthesia," N.Y. State J. M., Jun. 1953, pp. 1445-1448.

Ricci, et al., "Office Varicose Vein Surgery Under Local Anesthesia," J. Dermatol. Surg. Oncol., 1992, vol. 18, pp. 55-58.

Cohn, et al., "Ambulatory Phlebectomy Using the Tumescent Technique for Local Anesthesia," Dermatol. Surg. 1995, 21:315-318.

Ricci, et al., "Section I: Ricci-Georgiev Method," from "Ambulatory Phlebectomy: A Practical Guide for Treating Varicose Veins," Chap. 7, Sec. I, pp. 71-74, Mosby Year Book, Inc., St. Louis, MO 1995.

Goldman, "Section II: Goldman Method, Preparation and Dosage," from "Ambulatory Phlebectomy: A Practical Guide for Treating Varicose Veins," Chap. 7, Sec. II, pp. 74-76, Mosby Year Book, Inc., St. Louis, MO 1995.

Goldman et al., "High Ligation Division and Groin-to-Knee Stripping of the LSV: An Office Procedure," from "Ambulatory Phlebectomy: A Practical Guide for Treating Varicose Veins," Chap. 15, pp. 163-186, Mosby Year Book, Inc., St. Louis, MO 1995.

Smith, et al., "Tumescent Anesthesia in Ambulatory Phlebectomy," Dermatol. Surg., Apr. 1998, vol. 24:453-456.

Lamper, "Electrocoagulation in the Treatment of Varicose Subcutaneous Veins of the Lower Extremities," Khirurgiya, Nov. 1964, No. 11, pp. 93-96.

Proebstle, et al., "High Ligation and Stripping of the Long Saphenous Vein Using the Tumescent Technique for Local Anesthesia," Dermatol. Surg. 1998, vol. 24, pp. 149-153.

Stallworth, et al., "A Simplified and Efficient Method for Treating Varicose Veins," Surgery, Nov. 1979, pp. 765-768.

Bone Salat, "Phleboesthetic and Lymphedema Conference of the Spanish Society for Aesthetic Medicine," Medical Board of Madrid, Nov. 1998.

Bone Salat, "Fifth Hispano-Argentinean Conference on Advances in Aesthetic Medicine," Murcia, Oct. 1998.

Bone Salat, "Master's Thesis: Balearic University of Aesthetic Medicine," Palma de Mallorca, Oct. 1998.

Petrovsky, "Local Anesthesia," Big Medical Encyclopedia, 1974, 3rd Ed., vol. 1, pp. 534-536, Publishing House Soviet Encyclopedia, Moscow.

Vishnevsky, "Collected Papers," 1952, vol. 5, pp. 30-62, Academy of Medical Science of the USSR, Moscow.

Muranov, "Treatment of Varicose Veins of the Lower Extremity by the Endovascular Electrocoagulation Method," 1966, vol. 5, S.M. Kirov Academy of Military Medicine, Leningrad.

Welch, "History of Tumescent Anesthesia, Part I: From American Surgical Textbooks of the 1920s and 1930s," Sep. 1998, vol. 18, No. 5, pp. 353-357, Aesthetic Surgery Journal.

O'Reilly, "A Technique of Diathermy Sclerosis of Varicose Veins," 1981, vol. 51, No. 4, Aust. N.Z. J. Surg., pp. 379-382.

Sigel et al., "The Mechanism of Blood Vessel Closure by High Frequency Electrocoagulation," 1965, pp. 823-831, Surgery, Gynecology & Obstetrics.

Bone Salat, "Endoluminal Diode-Laser Treatment of Varicose Veins," Baron de Pinopar Medical Clinic, Jan. 1999, pp. 1-8.

Sedov et al., "Reducing Complications from Electrosurgical Treatment of Varicose Veins of the Lower Limbs," Department of Surgery, Drezna City Hospital, Moscow Region. Klin. Khir. Jul. 1980;(7):63-64.

O'Reilly et al., "Transcatheter Fiberoptic Laser Coagulation of Blood Vessels," Radiology 142: 777-780, Mar. 1982.

Drago, Mazza et al., "The Use of Argon Laser in the Treatment of Ideopathic Varices in the Lower Limbs," Minerva Angiologica, vol. 19, 1993.

Sattler, "Outpatient Surgery for Varicose Veins Under Tumescent Local Anaesthesia," presented at the World Congress of Phlebology, Sydney, Australia, Sep. 1998.

Korolenko, "Morphological Changes in Tissues After Novocain Solutions Are Injected Into Them Under Pressure," Medical Affairs, State Medical Publishing House, Ukrainian Soviet Socialist Republic, 1958.

Klein, "Tumescent Technique Chronicles: Local Anesthesia, Liposuction and Beyond," Dermatol. Surg. 1995:21, pp. 449-457.

Smith, "Tumescent Anesthesia in Ambulatory Phlebectomy," abstract presented at the Nov. 1997 Congress of the North American Society of Phlebology, Palm Desert, California.

VNUS Medical Technologies, "Endovenous Vein Shrinkage for the Treatment of Venous Insufficiency," slides presented at the Nov. 1997 Congress of the North American Society of Phlebology, Palm Desert, California.

Sommer et al., "Tumescent Local Anesthesia: Practical Application," pp. V-XIV, 40-44, 156-184, Dec. 8, 1998.

Transcript of Deposition of Mitchel P. Goldman, M.D. of Sep. 5, 2006; pp. 18-36.

* cited by examiner

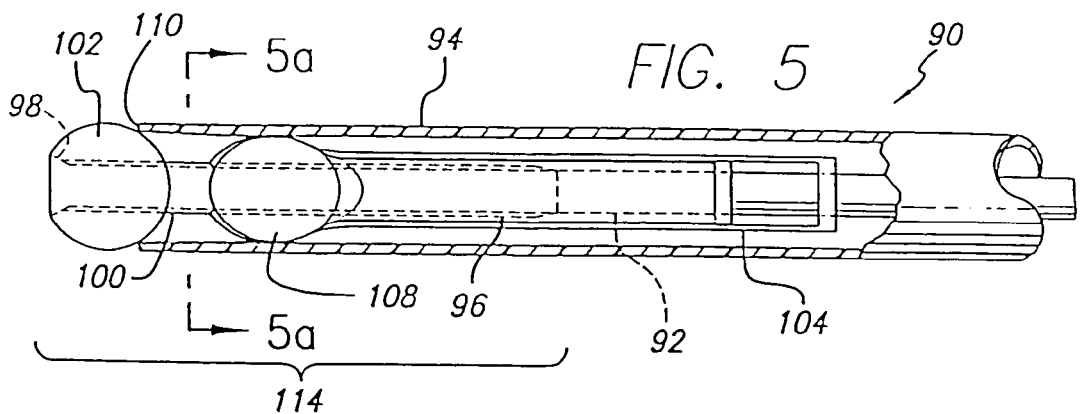
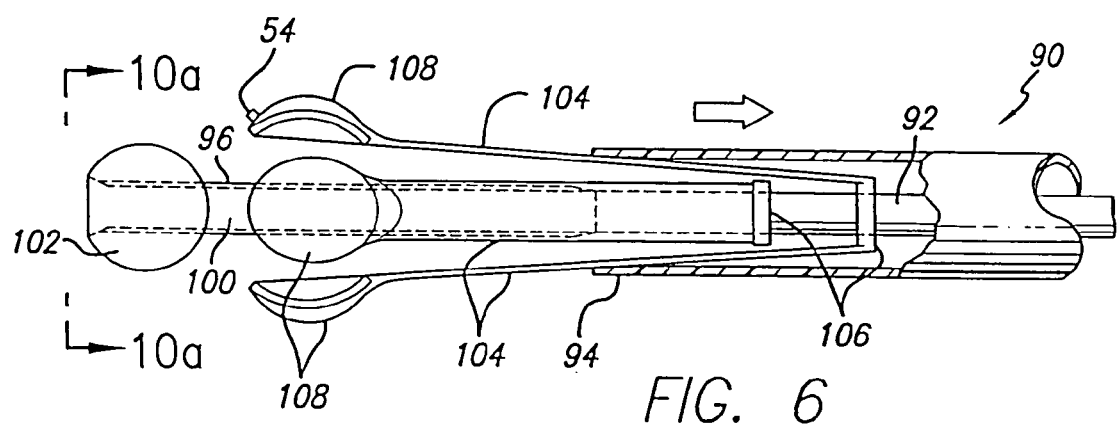
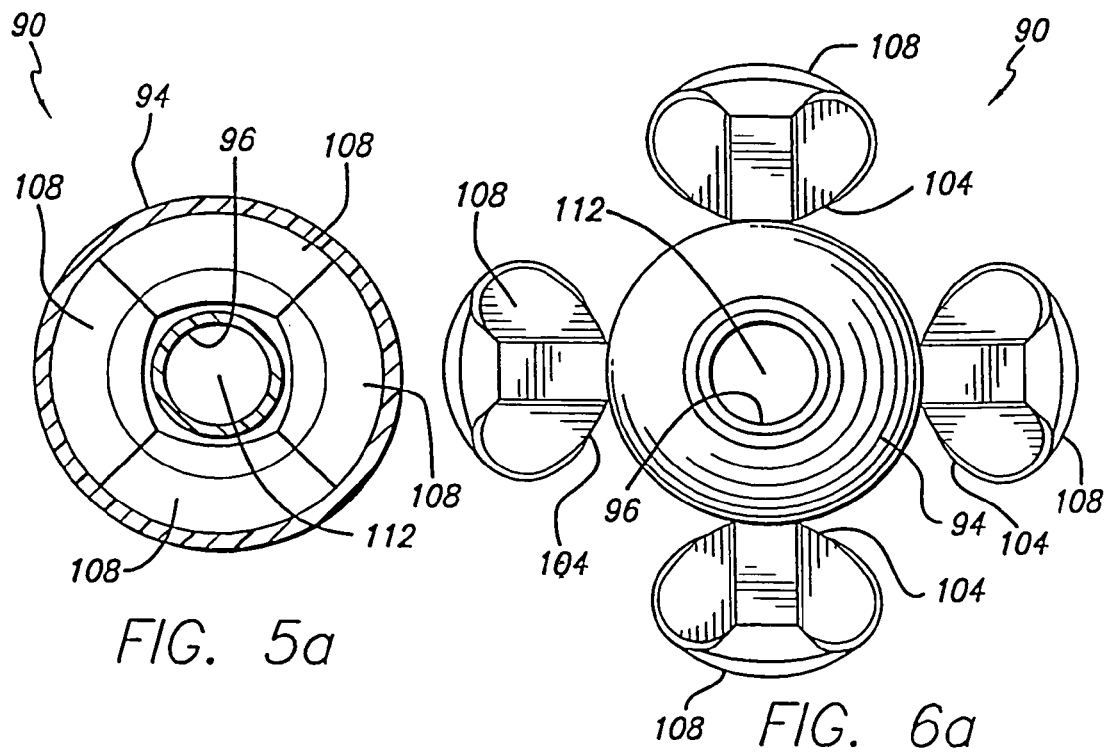

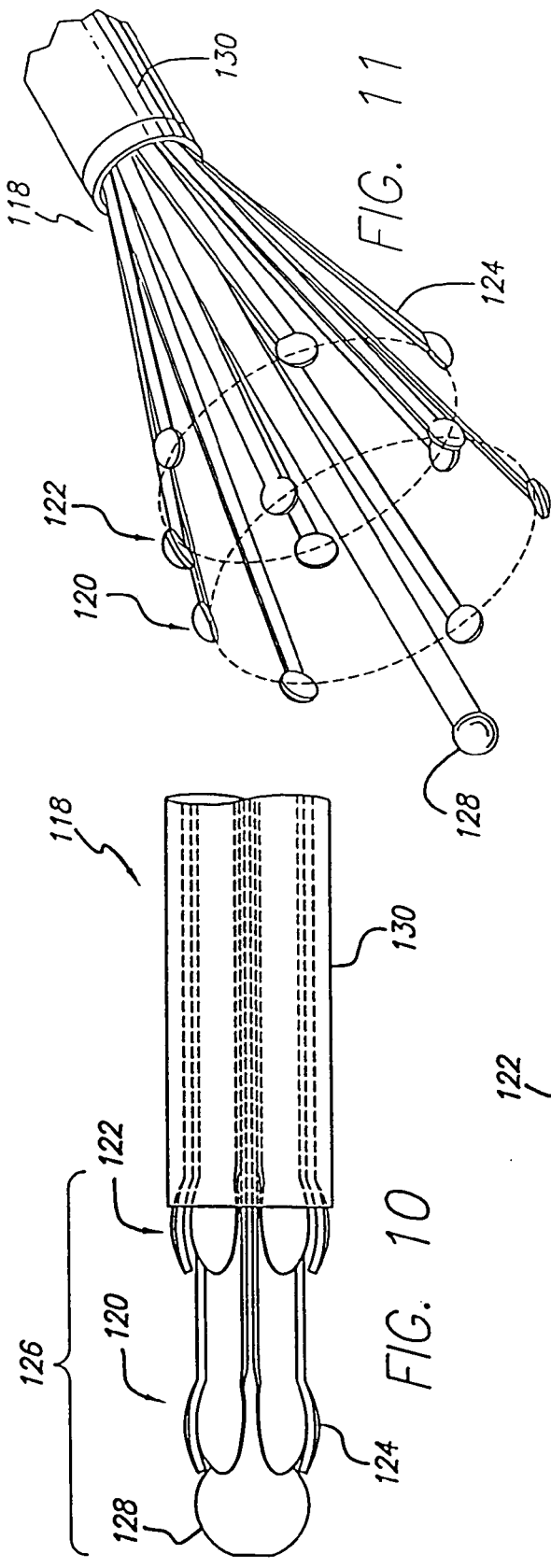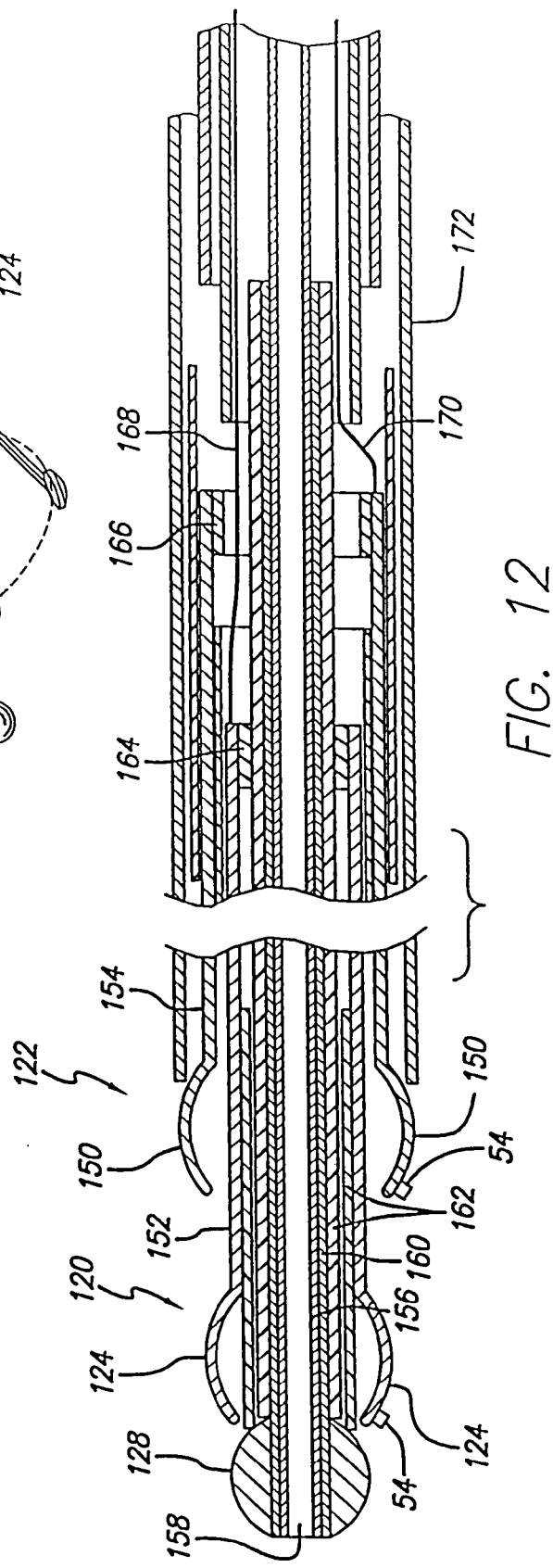

METHOD AND APPARATUS FOR APPLYING ENERGY TO BIOLOGICAL TISSUE INCLUDING THE USE OF TUMESCENT TISSUE COMPRESSION

This application is a continuation of application Ser. No. 09/899,885 (now U.S. Pat. No. 6,752,803) filed on Jul. 6, 2001, which is a continuation of application Ser. No. 09/267,127 (now U.S. Pat. No. 6,258,084) filed on Mar. 10, 1999, which is a continuation-in-part of application Ser. No. 09/138,472 (now U.S. Pat. No. 6,179,832) filed on Aug. 21, 1998, which is a continuation-in-part of application Ser. No. 08/927,251 (now U.S. Pat. No. 6,200,312) filed on Sep. 11, 1997 the disclosures of which are all hereby incorporated by reference.

BACKGROUND

The invention relates generally to a method and apparatus for applying energy to shrink a hollow anatomical structure, such as a fallopian tube or a vein, including but not limited to, superficial and perforator veins, hemorrhoids, and esophageal varices. In some particular aspects, the invention relates to a method for compressing an anatomical structure prior to the application of energy and apparatus including an electrode device having multiple leads for applying energy to the compressed structure to cause it to durably assume its compressed form.

The human venous system of the lower limbs consists essentially of the superficial venous system and the deep venous system with perforating veins connecting the two systems. The superficial system includes the long or great saphenous vein and the short saphenous vein. The deep venous system includes the anterior and posterior tibial veins which unite to form the popliteal vein, which in turn becomes the femoral vein when joined by the short saphenous vein.

The venous system contains numerous one-way valves for directing blood flow back to the heart such as those valves 20 located in the vein 22 shown in FIG. 1. The arrow leading out the top of the vein represents the antegrade flow of blood back to the heart. Venous valves are usually bicuspid valves, with each cusp 24 forming a sack or reservoir 26 for blood which, under retrograde blood pressure, forces the free surfaces of the cusps together to prevent retrograde flow of the blood and allows only antegrade blood flow to the heart. Competent venous valves prevent retrograde flow as blood is pushed forward through the vein lumen and back to the heart. When an incompetent valve 28 is in the flow path, the valve is unable to close because the cusps do not form a proper seal and retrograde flow of the blood cannot be stopped. When a venous valve fails, increased strain and pressure occur within the lower venous sections and overlying tissues, sometimes leading to additional valvular failure. Incompetent valves may result from the stretching of dilated veins. As the valves fail, increased pressure is imposed on the lower veins and the lower valves of the vein, which in turn exacerbates the failure of these lower valves. A cross-sectional perspective view of a dilated vein with an incompetent valve 28 taken along lines 2-2 of FIG. 1 is illustrated in FIG. 2. The valve cusps 24 can experience some separation at the commissure due to the thinning and stretching of the vein wall at the cusps. Two venous conditions which often result from valve failure are varicose veins and more symptomatic chronic venous insufficiency.

The varicose vein condition includes dilation and tortuosity of the superficial veins of the lower limbs, resulting in unsightly discoloration, pain, swelling, and possibly ulceration. Varicose veins often involve incompetence of one or more venous valves, which allow reflux of blood within the superficial system. This can also worsen deep venous reflux and perforator reflux. Current treatments of vein insufficiency include surgical procedures such as vein stripping, ligation, and occasionally, vein-segment transplant.

Chronic venous insufficiency involves an aggravated condition of varicose veins which may be caused by degenerative weakness in the vein valve segment, or by hydrodynamic forces acting on the tissues of the body, such as the legs, ankles, and feet. As the valves in the veins fail, the hydrostatic pressure increases on the next venous valves down, causing those veins to dilate. As this continues, more venous valves will eventually fail. As they fail, the effective height of the column of blood above the feet and ankles grows, and the weight and hydrostatic pressure exerted on the tissues of the ankle and foot increases. When the weight of that column reaches a critical point as a result of the valve failures, ulcerations of the ankle begin to form, which start deep and eventually come to the surface. These ulcerations do not heal easily because of poor venous circulation due to valvular incompetence in the deep venous system and other vein systems.

Other related venous conditions include dilated hemorrhoids and esophageal varices. Pressure and dilation of the hemorrhoid venous plexus may cause internal hemorrhoids to dilate and/or prolapse and be forced through the anal opening. If a hemorrhoid remains prolapsed, considerable discomfort, including itching and bleeding, may result. The venous return from these prolapsed hemorrhoids becomes obstructed by the anal sphincters, which gives rise to a strangulated hemorrhoid. Thromboses result where the blood within the prolapsed vein becomes clotted. This extremely painful condition can cause edema and inflammation.

Varicose veins called esophageal varices can form in the venous system with submucosa of the lower esophagus, and bleeding can occur from the dilated veins. Bleeding or hemorrhaging may result from esophageal varices, which can be difficult to stop and, if untreated, could develop into a life threatening condition. Such varices erode easily, and lead to a massive gastrointestinal hemorrhage.

Ligation of a fallopian tube (tubal ligation) for sterilization or other purposes is typically performed by laparoscopy. A doctor severs the fallopian tube or tubes and ties the ends. External cauterization or clamps may also be used. General or regional anesthetic must be used. All of the above are performed from outside the fallopian tube.

Hemorrhoids and esophageal varices may be alleviated by intra-luminal ligation. As used herein, "ligation" or "intra-luminal ligation" comprises the occlusion, collapse, or closure of a lumen or hollow anatomical structure by the application of energy from within the lumen or structure. As used herein, "ligation" or "intra-luminal ligation" includes electro-ligation. In the case of fallopian tube ligation, it would be desirable to perform the ligation from within the fallopian tube itself (intra-fallopian tube) to avoid the trauma associated with external methods.

Ligation involves the cauterization or coagulation of a lumen using energy, such as that applied through an electrode device. An electrode device is introduced into the lumen and positioned so that it contacts the lumen wall. Once properly positioned, RF energy is applied to the wall by the electrode device thereby causing the wall to shrink in cross-sectional diameter. In the case of a vein, a reduction in cross-sectional diameter of the vein, as for example from 5 mm (0.2 in) to 1 mm (0.04 in), significantly reduces the flow of blood through a lumen and results in an effective occlusion. Although not required for effective occlusion or ligation, the vein wall may completely collapse thereby resulting in a full-lumen obstruction that blocks the flow of blood through the vein. Likewise, a fallopian tube may collapse sufficiently to effect a sterilization of the patient.

One apparatus for performing ligation includes a tubular shaft having an electrode device attached at the distal tip. Running through the shaft, from the distal end to the proximal end, are electrical leads. At the proximal end of the shaft, the leads terminate at an electrical connector, while at the distal end of the shaft the leads are connected to the electrode device. The electrical connector provides the interface between the leads and a power source, typically an RF generator. The RF generator operates under the guidance of a control device, usually a microprocessor.

The ligation apparatus may be operated in either a monopolar or bipolar configuration. In the monopolar configuration, the electrode device consists of an electrode that is either positively or negatively charged. A return path for the current passing through the electrode is provided externally from the body, as for example by placing the patient in physical contact with a large low-impedance pad. The current flows between the ligation device and low impedance pad through the patient. In a bipolar configuration, the electrode device consists of a pair of electrodes having different potentials (such as a pair of oppositely-charged electrodes) of approximately equal size, separated from each other, such as by a dielectric material or by a spatial relationship. Accordingly, in the bipolar mode, the return path for current is provided by an electrode or electrodes of the electrode device itself. The current flows from one electrode, through the tissue, and returns by way of the another electrode.

To protect against tissue damage, i.e., charring, due to cauterization caused by overheating, a temperature sensing device is typically attached to the electrode device, although it may be located elsewhere. The temperature sensing device may be a thermocouple that monitors the temperature of the venous tissue. The thermocouple interfaces with the RF generator and the controller through the shaft and provides electrical signals to the controller which monitors the temperature and adjusts the energy applied to the tissue through the electrode device accordingly.

The overall effectiveness of a ligation apparatus is largely dependent on the electrode device contained within the apparatus. Monopolar and bipolar electrode devices that comprise solid devices having a fixed shape and size can limit the effectiveness of the ligating apparatus for several reasons. Firstly, a fixed-size electrode device typically contacts the vein wall at only one point or a limited arc on the circumference or inner diameter of the vein wall. As a result, the application of RF energy is highly concentrated within the contacting venous tissue, while the flow of RF current through the remainder of the venous tissue is disproportionately weak. Accordingly, the regions of the vein wall near the area of contact collapse at a faster rate than other regions of the vein wall, resulting in non-uniform shrinkage of the vein lumen. Furthermore, the overall strength of the occlusion may be inadequate and the lumen may eventually reopen. To avoid an inadequate occlusion, RF energy must be applied for an extended period of time so that the current flows through the tissue, including through the tissue not in contact with the electrode, generating thermal energy and causing the tissue to shrink sufficiently. Extended applications of energy have a greater possibility of increasing the temperature of the blood to an unacceptable level and may result in a significant amount of heat-induced coagulum forming on the electrode and in the vein which is not desirable. Furthermore, it is possible for the undesirable coagulum to form when utilizing an expandable electrode as well. This problem can be prevented by exsanguination of the vein prior to the treatment, as well as through the use of temperature-regulated power delivery. As used herein, "exsanguination" comprises the removal of all or some significant portion of blood in a particular area.

Secondly, the effectiveness of a ligating apparatus having a fixed-size electrode device is limited to certain sized veins. An attempt to ligate a vein having a diameter that is substantially greater than the fixed-size electrode device can result in not only non-uniform heating of the vein wall as just described, but also insufficient shrinkage of the vein diameter. The greater the diameter of the vein relative to the diameter of the electrode device, the weaker the energy applied to the vein wall at points distant from the point of electrode contact. Also, larger diameter veins must shrink a larger percentage for effective occlusion to occur. Accordingly, the vein wall is likely to not completely collapse prior to the venous tissue becoming over-cauterized at the point of electrode contact. While coagulation as such may initially occlude the vein, such occlusion may only be temporary in that the coagulated blood may eventually dissolve recanalizing the vein. One solution for this inadequacy is an apparatus having interchangeable electrode devices with various diameters. Another solution is to have a set of catheters having different sizes so that one with the correct size for the diameter of the target vein will be at hand when needed. Such solutions, however, are both economically inefficient and can be tedious to use. It is desirable to use a single catheter device that is usable with a large range of sizes of lumina.

A technique of reducing the diameter of the lumen of a vein at least close to the final desired diameter before applying energy to the vein has been found to aid in the efficiency of these types of procedures. The pre-reduction in vein diameter assists in pre-shaping the vein to be molded into a ligated state. The compression also exsanguinates the vein and forces blood away from the treatment site, thus preventing coagulation. One valuable technique employed is that of compressing the vein contained within a limb by applying external hydraulic pressure, via a pressure tourniquet, to the limb. Unfortunately there are some areas of the body to which a pressure tourniquet cannot be applied, such as the sapheno-femoral junction, which is above the thigh proximate the groin area. Furthermore, there are sites where a pressure tourniquet may be ineffective such as: the popliteal junction and other areas around the knee; and the ankle area (typically the posterior arch vein and some of the lower cockett perforators).

There exists a technique referred to as tumescent anesthesia that has been used in connection with liposuction procedures. The word "tumescent" means swollen or firm. This technique is accomplished by subcutaneously delivering into target fatty tissue a large volume of saline solution containing diluted Lidocaine and Epinephrine (adrenaline), a vasoconstrictive drug. The injected area then becomes locally anesthetized, and the adrenaline temporarily constricts the capillaries and other blood vessels. The tumescence-inducing fluid, or "tumescent fluid" is injected under pressure which causes the target fatty tissue to become swollen and firm. The tumescent fluid is typically pumped into the pocket of fat in order to numb the area, loosen the fat, and constrict the blood vessels to minimize bleeding or bruising in a liposuction procedure. The anesthetic and other agents in the tumescent solution should be allowed sufficient time to diffuse and take full effect throughout the target tissue. After surgery, patients may leave without assistance, and often return to their regular routine within several days. With the tumescent technique, postoperative discomfort is significantly reduced. The local anesthesia often remains in the treated tissue for 16 hours after surgery. Employing a technique of utilizing tumescent anesthesia in conjunction with ligation or radial lumen shrinkage less than ligation may provide benefits.

Although described above in terms of a vein, the concepts are generally applicable to other hollow anatomical structures in the body as well. The above description has been generally confined to veins in consideration of avoiding unnecessary repetition.

Hence those skilled in the art have recognized a need for an improved method and apparatus that can be used on areas of the body to shrink and ligate hollow anatomical structures. A need has also been recognized for an improved method and apparatus to pre-compress and exsanguinate a hollow anatomical structure while providing anesthetic and insulation benefits during the radial shrinkage of the hollow anatomical structure. The invention fulfills these needs and others.

SUMMARY OF THE INVENTION

The present invention is directed to a method and apparatus for applying energy to a hollow anatomical structure such as a vein, to shrink the structure. In a more detailed aspect, the invention is directed to pre-compressing and exsanguinating a hollow anatomical structure while providing anesthetic and insulation benefits during a procedure of shrinking the hollow anatomical structure.

In another aspect of the present invention, a method comprises providing fluid to tissue surrounding a hollow anatomical structure to induce tumescence of the tissue and consequent compression of the hollow anatomical structure during a procedure of applying energy to the hollow anatomical structure from within the structure. In a more detailed aspect, the method comprises introducing into the hollow anatomical structure a catheter having a working end and at least one electrode at the working end; placing the electrode into contact with the inner wall of the pre-compressed hollow anatomical structure and applying energy to the hollow anatomical structure at the treatment site via the electrode until the hollow anatomical structure durably assumes dimensions less than or equal to the pre-compressed dimensions caused by the injection of the solution into the tissue.

In another aspect in accordance with the invention, tumescent fluid is injected in the tissue surrounding the hollow anatomical structure along a selected length of the hollow anatomical structure. The electrode is then moved along a site within the selected length while continuously applying energy to result in a lengthy occlusion. In another approach, after an initial application of energy to one site internal to the hollow anatomical structure within the selected length, the electrode is moved down a given length of the hollow anatomical structure and energy is applied at that adjacent site. For the site where energy is applied, the hollow anatomical structure durably assumes dimensions less than or equal to the pre-compressed dimensions caused by the injection of the solution into the tissue.

In a more detailed aspect, tumescent anesthesia fluid is injected or otherwise provided to tissue contiguous with a vein to compress the vein to about a desired final diameter. A catheter having an energy application device, such as expandable electrodes, is introduced internal to the vein at a site within the compressed portion of the vein and energy is applied to the internal vein wall by the application device. Sufficient energy is applied to cause the vein to durably assume the compressed diameter such that when the effects of the tumescent anesthesia fluid are dissipated, the vein retains the compressed diameter.

Alternate means to prevent coagulum formation include fluid displacement of blood at the treatment site, or exsanguination by inducing self-constriction of the vessel. In the latter, self-constriction includes, but is not limited to, intraluminal delivery of a vasoconstrictive drug. Self-constriction also aids in pre-shaping the vein for ligation, as discussed previously. If the fluid delivered to the site is a sclerosant, the ligation effects would be further enhanced.

In further aspects, energy is applied to effectively occlude the treatment site. Further, the energy application device is moved along the treatment site while performing the step of applying energy so as to result in a lengthy occlusion of the treatment site. The treatment site may collapse around the energy application device as it is being moved. In yet further detail, fluid is delivered from within the hollow structure to the treatment site. This fluid may be used to exsanguinate the treatment site. Such fluid may be from the following group: saline; a vasoconstrictive agent; a sclerosing agent; a high impedance fluid; and heparin.

In another aspect, temperatures are sensed at two separate locations on the energy application device, and the temperature signals are averaged to determine the temperature at the site. In further detailed aspects, electrical energy is applied to the inner wall of the treatment site with an electrode, the electrode being in apposition with the inner wall. With the electrode being in apposition with the inner wall, the method further comprises the steps of applying electrical energy with the electrode to effectively occlude the treatment site at the electrode, and moving the electrode along the treatment site while maintaining the electrode in apposition with the vein wall while performing the step of applying energy to effectively occlude the treatment site so as to result in a lengthy effective occlusion of the treatment site. Sufficient energy is applied to collapse the hollow anatomical structure around the energy application device as it is being moved along the treatment site to result in a lengthy effective occlusion of the treatment site.

In yet a further aspect, apposition of the energy application device with the inner wall of the hollow anatomical structure is determined by monitoring the impedance experienced by the energy application device.

These and other aspects and advantages of the present invention will become apparent from the following more detailed description, when taken in conjunction with the accompanying drawings which illustrate, by way of example, embodiments of the invention.

BRIEF DESCRIPTION OF THE DRAWINGS

FIG. 5 is a cross-sectional view of the working end of an embodiment of a catheter in accordance with the invention depicting the electrodes in a fully retracted position;

FIG. 5a is an end view of the working end of the embodiment of the catheter taken along line 5a-5a of FIG. 5;

FIG. 6 is a cross-sectional view of the working end of the embodiment of the catheter of FIGS. 5 and 5a depicting the electrodes in a fully expanded position;

FIG. 6a is an end view of the working end of the embodiment of the catheter taken along line 6a-6a of FIG. 6;

FIG. 10 is a side view of an embodiment of an electrode catheter having two pluralities of longitudinally-separated expandable electrodes in a retracted condition;

FIG. 11 is a side view of the embodiment of the electrode catheter of FIG. 10 with both pluralities of the electrodes in expanded configurations; and FIG. 12 is a partial cross-sectional view of the embodiment of an electrode catheter of FIGS. 10 and 11.

DETAILED DESCRIPTION OF THE EMBODIMENTS

Figure 1:
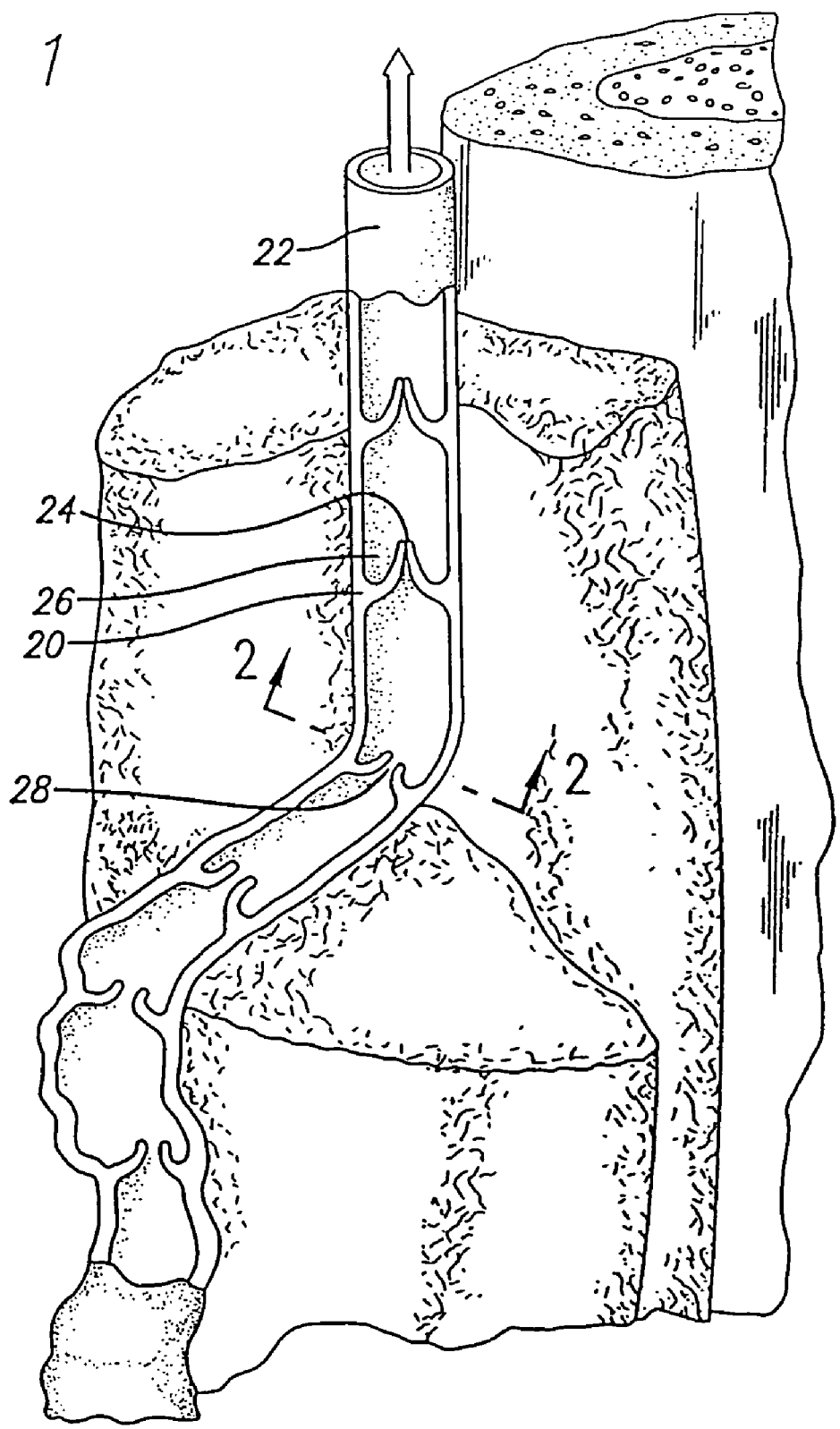
FIG. 1 shows a cross-sectional view of a vein having competent valves and having a dilated section with incompetent venous valves in a lower limb which are to be treated in accordance with the present invention.
Figure 2:
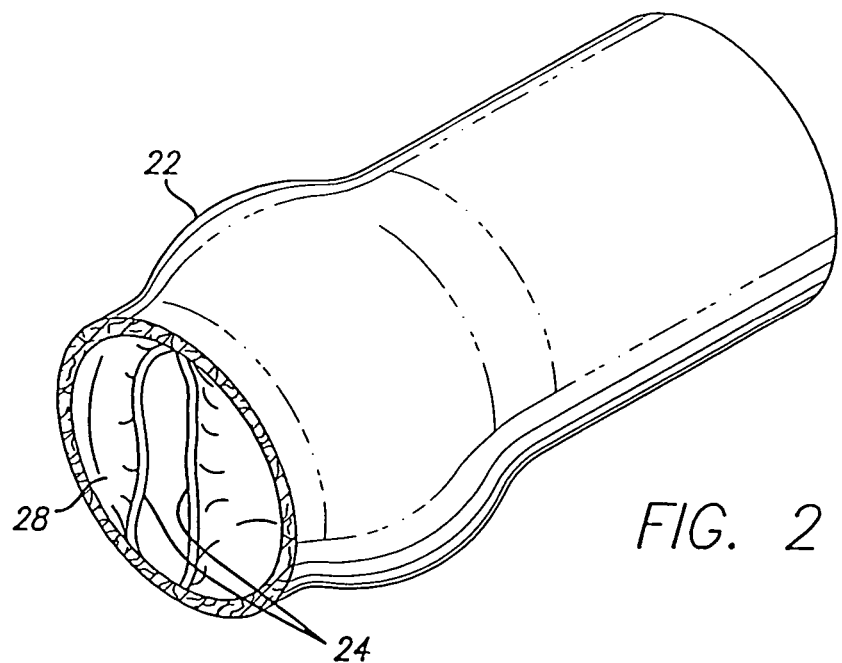
FIG. 2 shows a representative view of a venous section with an incompetent valve from FIG. 1 taken along lines 2-2 which is to be treated in accordance with the present invention.

As shown in the exemplary drawings, the invention is directed toward the intravenous treatment of veins using a catheter to deliver at least one electrode to a venous treatment site. As used herein, like reference numerals will designate similar elements in the various embodiments of the present invention to be discussed. In addition, unless otherwise noted, the term "working end" will refer to the direction toward the treatment site in the patient, and the term "connecting end" will refer to the direction away from the treatment site in the patient. The invention will be described in relation to the treatment of the venous system of the lower limbs. It is to be understood, however, that the invention is not limited thereto and may be employed intraluminally to treat veins in other areas of the body such as hemorrhoids, esophageal varices, and venous-drainage-impotence of the penis. Furthermore, although the invention will be described as using RF energy from the electrode, it is to be understood that other forms of energy such as microwaves, ultrasound, direct current, circulating heated fluid, radiant light, and lasers can be used, and that the thermal energy generated from a resistive coil or curie point element may be used as well.

Figure 3:
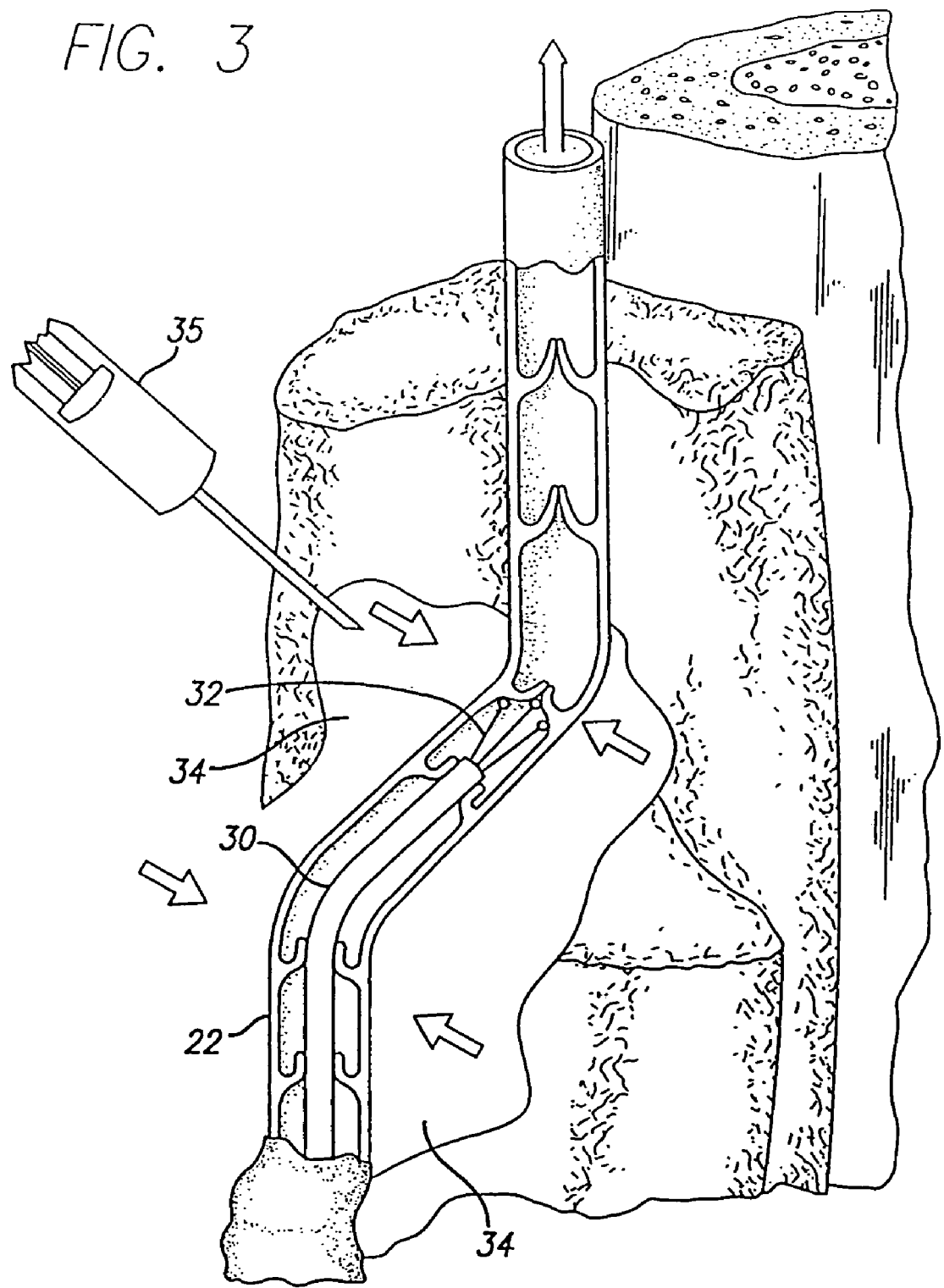
FIG. 3 is a cross-sectional view of the vein of FIG. 1 after the vein has been compressed, although not to full occlusion, by the injection of a tumescent anesthesia fluid in tissue surrounding the vein showing a catheter including an expandable electrode device prior to the application of energy to the vein.

Turning to FIG. 3, one preferred method of the present invention can be performed using the catheter 30 to deliver an expandable electrode device 32 (partially shown) to a venous treatment site in order to ligate the vein. Instead of compressing the tissue surrounding the treatment site via a pressure tourniquet, a tumescent anesthesia technique can be used to inject a dilute anesthetic and vasoconstrictive solution into the tissue surrounding the vein to be treated. The tumescent solution preferably includes mostly saline solution, with a local anesthetic such as Lidocaine, and a vasoconstrictive drug such as Epinephrine. The tumescent solution causes the surrounding tissue 34 to become swollen which compresses the vein 22, as indicated by the arrows, close to occlusion (in this case) or to occlusion. Sufficient tumescent solution should be delivered into the tissue surrounding the vein to compress and exsanguinate the vein. Before injecting the tumescent solution, the catheter 30 is placed within the vein at the treatment site, with the expandable electrode device retracted.

The solution is typically infused with a peristaltic pump. However, 60 cc or 100 cc syringes 35 can be used. Another alternative is an IV bag with a pressure cuff. Large volumes are typically delivered into the perivenal area via a large cannula. Sites are typically located 10 cm apart down the leg. Usually there are four or five delivery sites. The external result is a leg that appears inflated. The internal result is compressed veins plus an anesthetized leg. The expandable electrode device is then expanded into apposition with the venous tissue after compression of the vein. Energy such as high frequency RF energy is applied from the expandable electrode device to the venous tissue until the vein durably assumes dimensions less than or equal to the compressed dimensions caused by the injection of the tumescent solution into the tissue.

After completing the procedure for a selected venous section or treatment site, the electrode may be retracted and the catheter moved to another venous section where the ligation process is repeated. Ultrasound guidance can be used to monitor the progress of the procedure.

Figure 4:
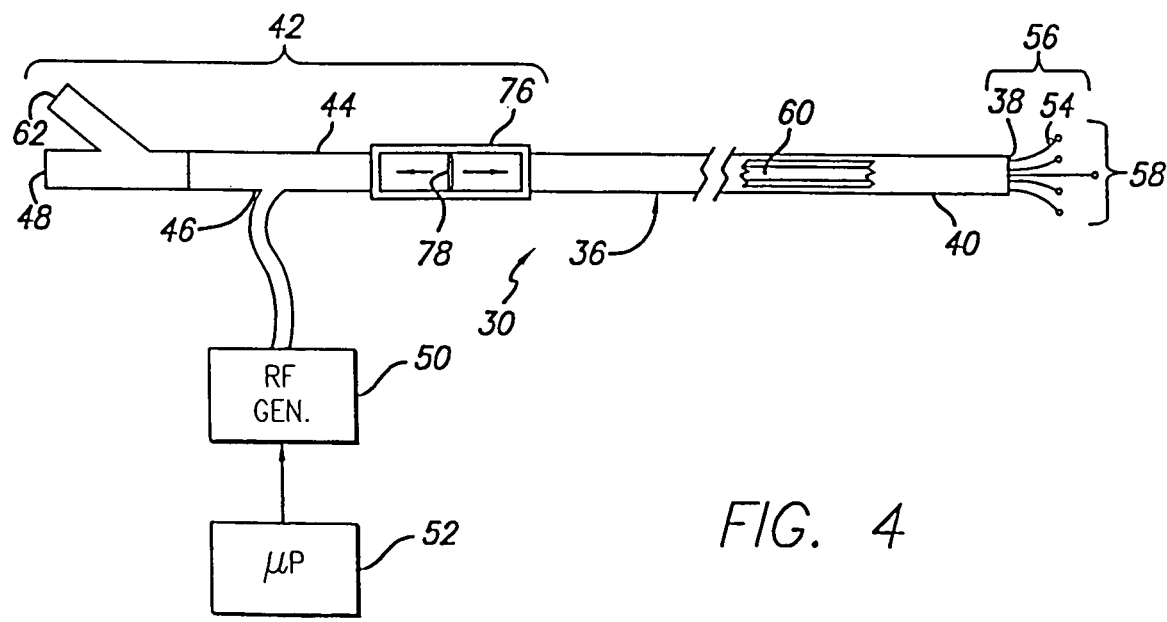
FIG. 4 is a diagram of an energy application system that may be used in conjunction with the method of the present invention, depicting a partial cutaway view of the first embodiment of the catheter showing both the working end and the connecting end with an RF generator and a microprocessor connected at the connection end.

One preferred embodiment of the catheter for delivering an expandable energy application device or expandable electrode device 56 to the venous treatment site is illustrated in FIG. 4. The catheter 30 includes an expandable energy application device 56 which in this embodiment, comprises an array of electrodes 58, an outer sheath 36 having a distal orifice 38 at its working end 40. The connector end 42 of the outer sheath is attached to a handle 44 that includes electrical connector 46. The handle additionally includes a guide wire port 48. The connector 46 is for interfacing with a power source, typically an RF generator 50, and a microprocessor controller 52. The power source and microprocessor controller are usually contained in one unit. The microprocessor controller controls the RF generator in response to external commands and data from a temperature sensor 54, such as a thermocouple, or temperature sensors that may be positioned at an intraluminal venous treatment site.

The catheter 30 includes the expandable electrode device 56 that moves in and out of the outer sheath by way of the distal orifice 38 in this embodiment, although in other embodiments the device 56 may expand from and contract into the catheter 30 at other locations. The expandable electrode device 56 includes a plurality of electrodes 58 which can be expanded by moving the outer sheath 36 relative to the electrodes. Although FIG. 4 illustrates a plurality of electrodes 58 surrounding a single central electrode, different electrode configurations may be used.

Contained within the outer sheath 36 is an inner sheath 60 or inner member as shown in the cutaway portion of FIG. 4. A fluid port 62 communicates with the interior of the outer sheath. The catheter 30 can be periodically flushed out with saline through the fluid port. The flushing fluid can travel between the outer sheath and the inner sheath. The fluid port also allows for the delivery of drug therapies. Flushing out the catheter prevents the buildup of biological fluid, such as blood, within the catheter. The treatment area or site of the vein can be flushed with a fluid such as saline, or a high impedance dielectric fluid, in order to evacuate blood from the treatment area of the vein so as to prevent the formation of coagulum or thrombosis. The use of a high impedance dielectric fluid can minimize unintended heating effects away from the treatment area. The dielectric fluid directs the current of RF energy toward the vein wall. In addition, a vasoconstrictive agent may be applied to shrink the vein, heparin may be applied for coagulation avoidance, and a sclerosing agent may be applied to assist in ligation. These drugs or agents may be applied before, during, or after the catheter is used to heat the vein wall.

In one preferred embodiment, the catheter 30 includes a lumen which begins at the distal tip 55, proximate the working end 40, and runs substantially along the axis of the inner member before terminating at the guide wire port 48 of the handle 44. A guide wire can be introduced through the lumen of the catheter for use in guiding the catheter to the desired treatment site. Where the catheter is sized to treat smaller veins, the outer diameter of the catheter may not allow for a fluid flush between the outer sheath and the inner sheath 60. However, a fluid flush can be introduced through the guide wire port 48 in such an embodiment.

Turning again to FIG. 4, an actuator 76 controls the extension of the electrode device 56 through the distal orifice 38. The actuator may take the form of a switch, lever 78, threaded control knob, or other suitable mechanism, and is preferably one that can provide fine control over the movement of the outer sheath 36 or the inner sheath 60, as the case may be. In one embodiment of the invention, the actuator interfaces with the outer sheath to move it back and forth relative to the inner sheath. In another embodiment the actuator interfaces with the inner sheath to move it back and forth relative to the outer sheath. The relative position between the outer sheath and inner sheath is thus controlled, but other control approaches may be used.

In a preferred embodiment of a catheter 90 is illustrated in FIG. 5. An inner member 92 or sheath is contained within the outer sheath 94. The inner sheath is preferably constructed from a flexible polymer such as polymide, polyethylene, or nylon, and can travel the entire length of the catheter. The majority of the catheter should be flexible so as to navigate the tortuous paths of the venous system. A hypotube having a flared distal end 98 and a circular cross-sectional shape is attached over the distal end of the inner sheath 92. The hypotube 96 is preferably no more than about two to three centimeters in length. The hypotube acts as part of a conductive secondary lead 100. An uninsulated conductive electrode sphere 102 is slipped over the hypotube. The flared distal end of the hypotube prevents the electrode sphere from moving beyond the distal end of the hypotube. The sphere is permanently affixed to the hypotube, such as by soldering the sphere both front and back on the hypotube. The majority of the surface of the electrode sphere remains uninsulated. The remainder of the hypotube is preferably insulated so that the sphere-shaped distal end can act as the electrode. For example, the hypotube can be covered with an insulating material such as a coating of parylene. The interior lumen of the hypotube is lined by the inner sheath 92 which is attached to the flared distal end of the hypotube by adhesive such as epoxy.

Surrounding the secondary lead 100 are a plurality of primary leads 104 that preferably have a flat rectangular strip shape and can act as arms. In one configuration, the strip shape is a width from 0.76 mm (0.03 in) to 1.00 mm (0.04 in) and a thickness of approximately 0.13 mm (0.005 in.). As illustrated in FIG. 6, the plurality of primary leads 104 is preferably connected to common conductive rings 106. This configuration maintains the position of the plurality of primary leads, while reducing the number of internal electrical connections. The conductive rings 106 are attached to the inner sheath 92. The position of the rings and the primary leads relative to the outer sheath 94 follows that of the inner sheath. As earlier described, the hypotube 96 of the secondary lead is also attached to the inner sheath. Two separate conductive rings can be used so that the polarity of different primary leads can be controlled separately. For example, adjacent primary leads can be connected to one of the two separate conductive rings so that the adjacent leads can be switched to have either opposite polarities or the same polarity. The rings are preferably spaced closely together, but remain electrically isolated from each other along the inner sheath. Both the rings and the hypotube are coupled with the inner sheath, and the primary leads that are connected to the rings move together with the secondary lead while remaining electrically isolated from the secondary lead. Epoxy or another suitable adhesive can be used to attach the rings to the inner sheath. The primary leads from the respective rings alternate with each other along the circumference of the inner sheath. The insulation along the underside of the leads prevents an electrical short between the rings. FIG. 6a illustrates an end view of the working end of catheter 90 taken along line 6a-6a of FIG. 6.

The conductive rings 106 and the primary leads 104 are attached together to act as cantilevers where the ring forms the base and the rectangular primary leads operate as the cantilever arms. The primary leads are formed to have an arc or bend such that the primary leads act as arms that tend to spring outwardly away from the catheter 90 and toward the surrounding venous tissue. Insulation along the underside of the primary leads and the conductive rings prevents unintended electrical coupling therebetween. Alternately, the primary leads are formed straight and connected to the conductive rings at an angle such that the primary leads tend to expand or spring radially outward from the conductive rings. The angle at which the primary leads are attached to the conductive rings should be sufficient to force the primary distal ends and their electrodes 108 through blood and into apposition with the vein wall 80 but not enough to preclude vein shrinkage. In particular, the primary leads 104 are formed with enough strength, and are mounted or bent such that they expand outwardly into apposition with the inner wall of the vein. However, the force they develop in an outward direction is not strong enough to prevent radial shrinkage of the vein. As the vein shrinks, due to the heating caused by the energy delivered by the electrodes 108, the shrinking vein causes a contraction of the primary electrodes. Due to the outward force constantly exerted by the primary leads 104, the electrodes 108 remain in constant apposition with the vein wall as it shrinks.

Other properties of the primary leads, such as lead shape and insulation thickness, affect the push force of the lead against the vein wall and the degree of arc or bend must be adjusted to compensate for these factors. The rectangular cross section of the primary leads can provide increased stability in the lateral direction while allowing the necessary bending in the radial direction. The primary leads are less likely to bend sideways when expanded outward due to the increased size of the rectangular lead in that sideways direction, and a uniform spacing between primary leads is more assured. Uniform spacing between the primary leads and the distal ends promotes uniform heating around the vein by the electrodes 108.

The distal ends of the primary leads 104 are uninsulated to act as the electrodes 108 having a rounded shape. In the embodiment shown, the shape is convex which may take the form of a spoon or hemispherical shape. The primary leads can be stamped to produce an integral shaped electrode at the distal end of the primary leads. The uninsulated outer portion of the distal end of the electrodes 108 which are to come into apposition with the wall of the vein is preferably rounded and convex. The flattened or non-convex inner portion of the distal end is insulated to minimize any unintended thermal effect, such as on the surrounding blood in a vein. The distal ends of the electrodes 108 are configured such that when the distal ends are forced toward the inner sheath 92, as shown in FIG. 5a, the distal ends combine to form a substantially spherical shape with a profile smaller than the spherical electrode 102 at the secondary distal end.

In one preferred embodiment as shown in FIG. 6, the electrodes 108 comprise a convex, square center section with semi-circular ends. It has been found that this "race track" configuration maximizes surface area of contact for the electrodes 108 shown.

The outer sheath 94 can slide over and surround the primary and secondary leads 100 and 104. The outer sheath includes an orifice 110 which is dimensioned to have approximately the same size as the spherical electrode 102 at the secondary distal end. A close or snug fit between the spherical electrode 102 and the orifice 110 of the outer sheath is achieved. This configuration provides an atraumatic tip for the catheter 90. The spherical electrode 102 is preferably slightly larger than the orifice 110. The inner diameter of the outer sheath is approximately the same as the diameter of the reduced profile of the combined primary distal end electrodes 108.

A fluid port (not shown) can communicate with the interior of the outer sheath 94 so that fluid can be flushed between the outer sheath and inner sheath 92 as described above. Alternately, a fluid port can communicate with a central lumen 112 in the hypotube which can also accept a guide wire for use in guiding the catheter to the desired treatment site. It is to be understood that another lumen can be formed in the catheter to deliver fluid to the treatment site. The delivered fluid displaces or exsanguinates blood from the vein so as to avoid heating and coagulation of blood. The delivery of a dielectric fluid increases the surrounding impedance so that RF energy is directed into the tissue of the vein wall. An alternate fluid could be a sclerosing agent which could serve to displace blood or to further enhance occlusion of the vein when applied before, during, or after energy delivery. The fluid can also include an anticoagulant such as heparin which can chemically discourage the coagulation of blood at the treatment site. The catheter 90 can be periodically flushed with saline which can prevent the buildup of biological fluid, such as blood, within the catheter. The saline can be flushed through the central lumen 112 or between the inner and outer sheaths. If a central lumen is not desired, the lumen of the hypotube can be filled with solder.

The electrode device 114 can operate in either a bipolar or a monopolar configuration. When adjacent primary leads have opposite polarity, a bipolar electrode operation is available. When the primary leads are commonly charged a monopolar electrode operation is available in combination with a large return electrode pad placed in contact with the patient. When the primary electrodes 108 are commonly charged or have a first potential, and a secondary electrode 102 has an opposite polarity or different potential, a bipolar electrode operation is available. More or fewer leads may be used. The number of leads can be dependent on the size or diameter of the vein to be treated, as described above.

Although not shown, it is to be understood that the catheter 90 can include one or more temperature sensors, such as thermocouples, mounted in place on an electrode 108 so that the sensor is substantially flush with the exposed surface of the electrode 108. (The sensor is shown in a raised position in the drawings for clarity of illustration only). The temperature sensor senses the temperature of the portion of the vein that is in apposition with the exposed electrode 108 surface. The sensor provides an indication of when shrinkage occurs (70 degrees C. or higher). Application of RF energy from the electrodes 108 is halted or reduced when the monitored temperature reaches or exceeds the specific temperature that was selected by the operator, such as the temperature at which venous tissue begins to cauterize. Other techniques such as impedance monitoring and ultrasonic pulse echoing can be utilized in an automated system which shuts down or regulates the application of RF energy from the electrodes to the venous section when sufficient shrinkage of the vein 22 is detected. This also helps to forestall overheating of the vein.

Figure 7:
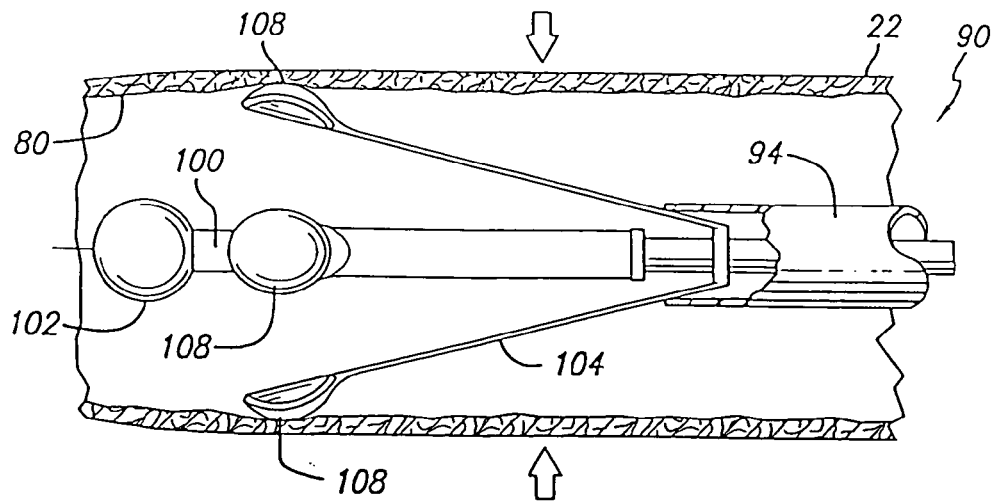
FIG. 7 is a cross-sectional view of a vein after the vein has been compressed, although not to full occlusion, by tumescent anesthesia fluid, the vein containing the catheter of FIG. 5 with the electrodes in apposition with the vein.
Figure 8:
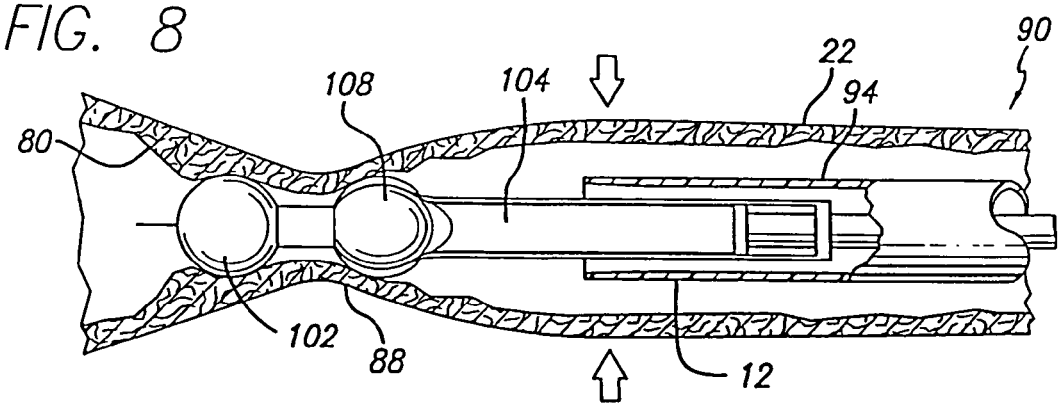
FIG. 8 is a cross-sectional view of the compressed vein containing the catheter of FIG. 5 where the vein is being ligated by the application of energy from the electrodes.

Referring now to FIGS. 7 and 8, in the operation of this embodiment of a catheter 90, the catheter is inserted into a vein 22. Fluoroscopy, ultrasound, an angioscope imaging technique, or another technique may be used to direct and confirm the specific placement of the catheter in the vein. Impedance measurements can also be used to determine proper positioning of the catheter, particularly at the ostium of a vessel such as at the sapheno-femoral junction. The impedance will be low when the electrodes are in the blood stream. The catheter can then be moved until a high impedance value is obtained, indicating electrode contact with the vein wall. The vein wall 80 has been compressed by the introduction of tumescent anesthesia into the tissue surrounding the vein as indicated by the arrows. The arrows in the figures indicate the compression of the tissue. Unless stated otherwise, all drawing figures having arrows indicating tissue compression are not drawn to scale for purposes of clarity of illustration and are meant to be representations of the vein in a nearly fully occluded state.

The reduction in the vein 22 diameter caused by the tumescence of the tissue in contact with the treatment site assists in pre-shaping the vein to be molded to a ligated state. The compression also exsanguinates the vein and forces blood away from the treatment site, thus preventing coagulation.

The actuator 76 (FIG. 4) is then operated to retract the outer sheath 94 to expose leads the 100 and 104. As the outer sheath no longer restrains the leads, the primary leads 104 move outward relative to the axis defined by the outer sheath, while the secondary lead 100 remains substantially linear along the axis defined by the outer sheath. The primary leads continue to move outward until their electrodes 108 are placed in apposition with the vein wall 80 and the outward movement of the primary leads is impeded. The primary electrodes 108 contact the vein wall along a generally circumferential area or band of the vein wall. This outward movement of the primary leads occurs in a substantially symmetrical fashion so that the primary electrodes 108 are substantially evenly spaced. Alternately, the electrodes 86 can be spaced apart in a staggered fashion such that they do not lie in the same plane. For example, the adjacent electrodes 86 can extend different lengths from the catheter so that a smaller cross-sectional profile is achieved when the electrodes 86 are collapsed toward one another.

When the electrodes 102 and 108 are positioned at the treatment site of the vein, the RF generator 50 is activated to provide suitable RF energy. One suitable frequency is 510 kHz. One criterion used in selecting the frequency of the energy to be applied is the control desired over the spread, including the depth, of the thermal effect in the venous tissue. Another criterion is compatibility with filter circuits for eliminating RF noise from thermocouple signals. In a bipolar operation, the primary electrodes 108 are charged with one polarity opposite that of the secondary electrode 102. The coupling between oppositely charged primary and secondary electrodes produces RF fields therebetween, and form a symmetrical RF field pattern along a circumferential band of the vein wall 80 to achieve a uniform temperature distribution along the vein wall being treated.

The RF energy produces a thermal effect which causes the venous tissue to shrink, reducing the diameter of the vein 22. The thermal effect produces structural transfiguration of the collagen fibrils in the vein. The collagen fibrils shorten and thicken in cross-section in response to the heat from the thermal effect. As shown in FIG. 8, the energy causes the vein wall 88 to collapse until further collapse is impeded by the primary lead electrodes 108. The primary lead electrodes are pressed closer together by the shrinking vein wall and assume a reduced profile shape which is sufficiently small so that the vein is effectively ligated.

Figure 9:
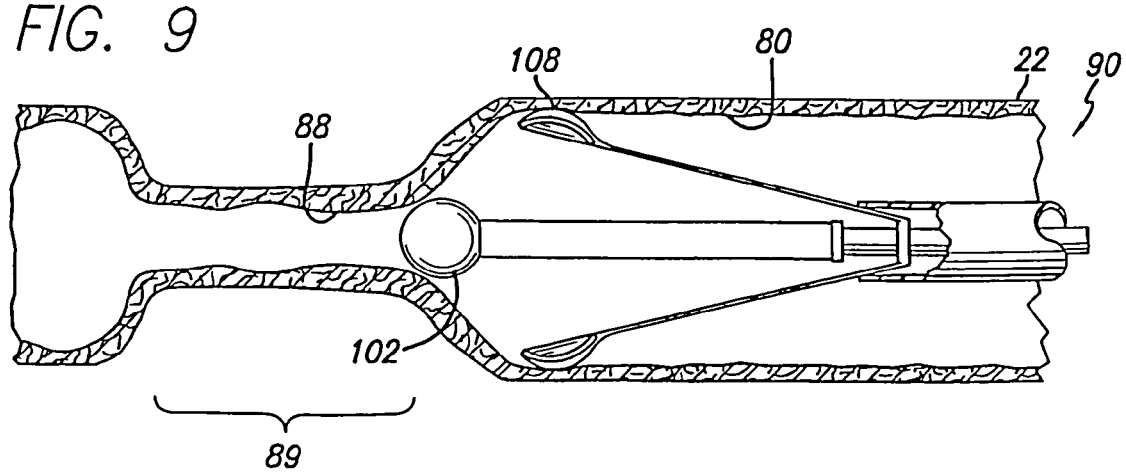
FIG. 9 is a partial cross-sectional view of the vein wall of FIG. 8 showing a lengthy effective occlusion made by moving the electrodes along the treatment site of the vein while maintaining the electrodes in apposition and continuing to apply energy to the vein wall.

The catheter 90 is pulled back while continuing energy delivery as shown in FIG. 9. Ligation as the catheter is being retracted produces a lengthy occlusion 89 which is stronger and less susceptible to recanalization than an acute point occlusion.

In a monopolar operation, the secondary-lead electrode 102 remains neutral, while the primary electrodes 108 are commonly charged and act in conjunction with an independent electrical device, such as a large low-impedance return pad (not shown) placed in external contact with the body, to form RF fields substantially evenly spaced around the circumference of the vein. The thermal effect produced by those RF fields along the axial length of the vein wall 80 causes the vein wall to collapse around the primary lead electrodes. The electrode device is retracted as described in the bipolar operation.

In either bipolar or monopolar operation the application of RF energy is substantially symmetrically distributed through the vein wall, as previously described. The electrodes should be spaced no more than 4 or 5 millimeters apart along the circumference of the vein wall 80, which defines the target vein diameter for a designed electrode catheter. Where the electrodes are substantially evenly spaced in a substantially symmetrical arrangement, and the spacing between the electrodes is maintained, a symmetrical distribution of RF energy increases the predictability and uniformity of the shrinkage and the strength of the occlusion.

Although not shown, in another embodiment, the primary leads may be mounted or otherwise configured such that they expand outwardly in an asymmetrical fashion. One purpose for an asymmetrical electrode arrangement is to only shrink a portion of the vein wall to achieve occlusion. Such may be desired in the case of preferentially shrinking a tributary branch or aneurysm on one side of the vein.

After completing the procedure for a selected venous section or treatment site, the actuator 76 causes the primary leads 104 to return to the interior of the outer sheath 94. Once the primary leads are within the outer sheath, the catheter 90 may be moved to another venous section where the ligation process is repeated.

As illustrated in FIGS. 10 and 11, another embodiment of an expandable electrode catheter 118 includes two sets of expandable electrode leads 120 and 122, although additional sets of electrode leads may be possible. The electrodes 124 of this embodiment are similar to the electrodes of the embodiment illustrated in FIG. 6 having electrodes with a rounded, convex, spoon-shaped contact area. Other shapes for the electrode may be used, such as ellipses, rounded, ovals, race tracks, and others. Although only one electrode is indicated by numeral 124 in FIGS. 10 and 11, this is for purposes of clarity in the drawings only. All electrodes are meant to be indicated by numeral 124. While each set of electrode leads may include as few as two electrode leads, the illustrated embodiment includes six electrode leads per set, although more than six electrode leads may be used as well.

In the embodiment shown in FIGS. 10 and 11, the sets of electrode leads 120 and 122 are longitudinally separated from each other. Thus, the electrodes within each set of electrode leads are separated from one another radially and each of those electrodes is also separated from every electrode in the other set longitudinally, due to the longitudinal separation. There therefore exists radial separation and longitudinal separation of electrodes at the working end 126 of the catheter 118 in the arrangement shown in FIGS. 10 and 11.

With the configuration of electrode leads presented in FIGS. 10 and 11, greater flexibility exists in establishing current flows through the tissue of a patient. As in previous embodiments, the electrodes expand outwardly into contact with patient tissue. Where all the electrodes of a first set of electrode leads have the same polarity, there may be an odd number of electrodes in the set, or an even number. All electrodes in the set may be connected to a common connection point, such as the conducting ring 106 shown in FIG. 6. A single conductor from the connecting end of the catheter may power all electrodes of the set by a single connection to that conducting ring. All electrodes of a second set of electrode leads may also be commonly connected at a respective conducting ring but to a different electrical potential than the first set. Because two different electrical potentials exist at the working end of the catheter, energy will flow through the patient tissue between those sets of electrode leads and a bipolar arrangement will exist. Thus, a length of patient tissue, at least as long as the distance between the first and second sets of electrode leads, will receive the energy.

A monopolar arrangement may also be established if desired by setting all electrodes of all electrode leads to the same electrical potential and establishing a different electrical potential outside the patient, such as at a "backplate" in contact with the skin of the patient at a selected location. Energy from the working end 126 of the catheter will then flow through the patient to the return provided by the backplate.

In another arrangement in polarizing or controlling the electrical potential at the electrodes, the electrodes in the first set of electrode leads may be individually controlled so that there are electrode pairs of differing potentials in the set of leads. This would establish a bipolar approach within the first set of leads itself. If the electrodes of the second set of leads are likewise connected for different potentials among themselves, they too would provide a bipolar approach in their own set and currents would flow through patient tissue between the electrodes in each set of leads. If the electrodes having a first polarity in the first set are aligned with the electrodes having a different polarity in the second set of leads, energy would not only flow between the bipolar electrodes within the set but would also flow to the electrodes in the other set resulting in two bipolar arrangements at the single working end of the catheter. Patient tissue of a length at least as great as the distance between the first and second sets of electrode leads will receive energy as well as patient tissue between electrodes within each set of leads itself.

A further arrangement coupled with the bipolar approach just described would be to also use a backplate at a different electrical potential to provide further control over the energy flow through the patient's tissue. In this case, energy would flow between the electrodes within each set of leads, between electrodes in different sets of leads, and between electrodes and the backplate.

In yet a further arrangement, each of the electrodes may be individually connected to a power source (50, FIG. 4) and the electrical potential at each electrode can be individually controlled. This arrangement may yield even more precise control over the current densities through patient tissue. As an example, where less current flow is desired between certain electrodes of a set of leads but more current flow is desired between those electrodes and electrodes of a second set of leads, the potential between the electrodes of the same set may be reduced but the potential between those electrodes and the electrodes of the second set of leads may be increased resulting in the desired current flow densities. In the case where a backplate is also used, the electrodes may be controlled so that energy flows between such electrodes and the backplate. Because each electrode is individually controlled, the level of energy it imparts to the tissue at its location is controllable.

One factor that could affect the number of electrodes per set of electrode leads is the diameter of the vein being treated. The design of the contact pad for the electrode leads could also affect the desired number of electrodes for a given procedure.

In this embodiment, the electrode leads 120, 122 are formed to expand outwardly into apposition with the target tissue, yet as the target tissue shrinks, the electrodes maintain contact with that tissue and are moved inwardly by that tissue. Because of this arrangement, the leads compensate for variations in the diameter of the vein. They are therefore capable of maintaining apposition with the tissue whether or not compression of the vein or anatomical structure exists, such as by use of a pressure cuff or tourniquet or tumescence of the surrounding tissue.

The tip 128 of the electrode catheter 118 should have a hemispherical or another atraumatic shape. The tip 128 may be electrically neutral, and may be fabricated from a polymer or it may be fabricated of stainless steel. Because the tip 128 has a rounded shape and is located at the distal extreme of the catheter, it may perform a guiding function when introducing the catheter to the patient.

The double set of expandable electrodes can be used to ligate veins or other hollow anatomical structures in a manner similar to that previously described. The outer sheath 130 can be pulled back to allow the electrode to expand outwardly from the catheter and into apposition with the wall of the lumen being treated. The two sets of electrodes 120 and 122 apply energy to the lumen to cause it to shrink to a reduced diameter. The catheter can be moved or pulled back while the energy is being applied to treat an extended area of the lumen. When the desired area of the lumen or vein is treated (e.g., ligated) energy is no longer provided to the electrodes, and the outer sheath 130 is pushed forward to force the expanded electrodes back to an unexpanded condition. The catheter can then be removed from the patient, or another section of the vein can be treated.

The description of the component parts discussed above are for a catheter to be used in a vein ranging in size from 3 mm (0.12 in) to 10 mm (0.39 in) in diameter. It is to be understood that these dimensions do not limit the scope of the invention and are merely exemplary in nature. The dimensions of the component parts may be changed to configure a catheter that may used in various-sized veins or other anatomical structures.

Referring now to FIG. 12, there is shown a partial cross-section view of the catheter of FIGS. 10 and 11. Two pluralities of electrodes 120 and 122 are shown with the electrodes of the first plurality 120 being indicated by numeral 124 and the electrodes of the second plurality 122 being indicated by numeral 150. Each electrode is formed from an electrically-conductive electrode lead 152 and 154 respectively that is electrically insulated along its length except at its distal end at which point no insulation exists thus forming the electrode. Each lead has an outward bend (not shown). An inner tube 156 includes a lumen 158 through which fluid may flow for flush or other purposes, or through which a guide wire may be positioned. A hypotube 160 is positioned over the inner tube and layers of insulation 162 are mounted over the hypotube. The first plurality 120 of electrode leads 152 extend proximally to a first mounting ring 164 to which all are connected. The second plurality 122 of electrode leads 154 extend proximally to a second mounting ring 166 to which all are connected. The rings 164 and 166 are mounted over the hypotube insulation so that no electrical conduction path exists between the two. Wire conductors 168 and 170 extend from the proximal end of the catheter to each ring so that all electrode leads connected to a particular ring are interconnected electrically.

Alternate arrangements are possible and in one, alternating electrodes of a particular plurality are connected to two different rings. Each ring is separately connected to the power source and the polarities of the rings may therefore be made different to establish a bipolar approach within the plurality. One electrode may be a "+" polarity while the two adjacent electrodes may be a "−" polarity. In this case then, there would be a total of three rings for all electrodes. In another arrangement, both pluralities would have two rings for its respective electrodes with alternating electrodes connected to different rings so that bipolar approaches within each plurality may be established. In this case, there would exist a total of four rings for the two pluralities of electrodes.

An outer movable sheath 172 when slid in the distal direction to the point shown in FIG. 12 will cause the electrode leads to contract to the position shown. When slid in the proximal direction a sufficient distance, the sheath 172 acts as a deployment device in that it will move past the bend (not shown) in each of the electrode leads of the second plurality 122 permitting all electrode leads to expand outwardly as shown in FIG. 11.

The electrode leads are formed of stainless steel in this embodiment and with the thin insulation layer and the outward bend, have enough strength to automatically move outwardly through blood flow (in a venous application) and into apposition with the inner wall of the target tissue. As the inner wall shrinks due to the application of heat by the electrodes, the inner wall will force the electrode leads toward their contracted position but the electrodes will automatically stay in apposition with the inner wall during the entire ligation process due to their outward bends and the material of which they are formed.

In one embodiment shown in FIG. 12, the electrode 124 includes a temperature sensor 54 and an electrode of the second plurality also includes a temperature sensor 54. Although not shown as such, they are mounted flush with the outer electrode surfaces and their wires protrude inwardly through the electrode and are held in place along the respective leads 152 and 154. In one embodiment, the microprocessor 52 (FIG. 4) receives the signals from both temperature sensors, averages those signals and determines the effective temperature at the treatment site based on that average signal. Methods of averaging temperature signals are well known to those skilled in the art and no further description is provided here.

Although described above as positively charged, negatively charged, or as a positive conductor or negative conductor, these terms are used for purposes of illustration only. These terms are generally meant to refer to different electrode potentials and are not meant to indicate that any particular voltage is positive or negative. Furthermore, other types of energy such as light energy from fiber optics can be used to create a thermal effect in the hollow anatomical structure undergoing treatment. Additionally, although the electrodes and leads have been described as protruding from a distal orifice in the catheter, they may be expanded by other means and in other configurations. In another embodiments, the leads may be deployed by an inner pull wire, hydraulics, or magnetic fields.

The benefits of tumescence would include locally anesthetizing the treatment area for a prolonged period of time and insulating most of the surrounding tissue and nerves from the damage of heat conducting from the treated vein. An additional benefit of the vasoconstriction induced by the Epinephrine would be that the constricted blood vessels would limit how fast the body absorbed the Lidocaine thus keeping the level of Lidocaine absorbed below the toxicity level. Also, as mentioned supra, extended applications of energy have a greater possibility of increasing the temperature of the blood to an unacceptable level and may result in a significant amount of heat-induced coagulum forming on the electrode and in the vein which is not desirable. Using a tumescent anesthesia compression technique, including the administration of vasocontrictive drugs, would aid in preventing this problem by exsanguinating the vein.

Although described above in terms of a vein, the concepts are generally applicable to other hollow anatomical structures in the body as well. The above description has been generally confined to veins in consideration of avoiding unnecessary repetition.

While several particular forms of the invention have been illustrated and described, it will be apparent that various modifications can be made without departing from the spirit and scope of the invention. Accordingly, it is not intended that the invention be limited, except as by the appended claims.

What is claimed is:

1. A method of applying energy to a hollow anatomical structure comprising the steps of:
   introducing an elongate member into the hollow anatomical structure;
   advancing the elongate member within the hollow anatomical structure;
   positioning a distal end of the elongate member at or near a treatment site within the hollow anatomical structure;
   administering fluid around the hollow anatomical structure at the treatment site to cause the wall of the hollow anatomical structure to move towards the distal end of the elongate member; and
   applying energy to the hollow anatomical structure at the treatment site from the distal end of the elongate member.

2. The method of claim 1, further comprising the step of moving the distal end of the elongate member along the hollow anatomical structure during the step of applying energy.

3. The method of claim 1 further comprising the steps of:
   ceasing the step of applying energy;
   moving the distal end of the elongate member to a new treatment site along the hollow anatomical structure;
   applying energy to the hollow anatomical structure at the new treatment site from the distal end of the elongate member.

4. The method of claim 1 wherein the step of applying energy includes the step of applying electrical energy.

5. The method of claim 1 wherein the step of applying energy includes the step of applying RF energy.

6. The method of claim 1 wherein the step of applying energy includes the step of applying microwave energy.

7. The method of claim 1 wherein the step of applying energy includes the step of applying light energy.

8. The method of claim 1 wherein the step of applying energy includes the step of applying thermal energy.

9. The method of claim 1 wherein the fluid thermally insulates the tissue near the treatment site.

10. The method of claim 1 wherein the fluid thermally insulates nerve tissue near the treatment site.

11. The method of claim 1 wherein the fluid limits thermal damage to the tissue near the treatment site during the step of applying energy.

12. The method of claim 1 wherein a sufficient volume of fluid is administered to cause the tissue surrounding the hollow anatomical structure at the treatment site to become tumescent.

13. The method of claim 1 further comprising the step of extending electrodes from the distal end of the elongate member at the treatment site before the step of applying energy.

14. The method of claim 1, wherein the hollow anatomical structure comprises a vein in a lower limb.

15. The method of claim 1, wherein the elongate member comprises a catheter.

16. The method of claim 15, wherein applying energy comprises applying RF energy.

17. The method of claim 16, wherein the hollow anatomical structure comprises a vein in a lower limb.

18. The method of claim 8, further comprising generating the thermal energy with a resistive coil.

19. The method of claim 18, wherein the hollow anatomical structure comprises a vein in a lower limb.

20. The method of claim 18, wherein the elongate member comprises a catheter.

21. The method of claim 1, wherein the elongate member comprises a fiber optic.

22. The method of claim 21, wherein applying energy comprises applying light energy.

23. The method of claim 22, wherein the hollow anatomical structure comprises a vein in a lower limb.

24. The method of claim 1, wherein administering fluid at the treatment site comprises administering tumescent fluid solution into tissue around the hollow anatomical structure and thereby compressing the hollow anatomical structure sufficiently to exsanguinate blood from the hollow portion of the hollow anatomical structure at the treatment site.

25. The method of claim 1, wherein administering fluid at the treatment site comprises administering fluid into the tissue surrounding the hollow anatomical structure to cause swelling and compress the hollow anatomical structure to a reduced size around the elongate member.

* * * * *

UNITED STATES PATENT AND TRADEMARK OFFICE
CERTIFICATE OF CORRECTION

| | | |
|---|---|---|
| PATENT NO. | : 7,396,355 B2 | |
| APPLICATION NO. | : 10/872646 | |
| DATED | : July 8, 2008 | |
| INVENTOR(S) | : Goldman et al. | |

It is certified that error appears in the above-identified patent and that said Letters Patent is hereby corrected as shown below:

On the Title page, column 2, first line under OTHER PUBLICATIONS (Approx.), delete "et al," and insert -- et al., --, therefor.

On Title page 2, column 1, first line under OTHER PUBLICATIONS (Approx.), delete "et al," and insert -- et al., --, therefor.

On Title page 2, column 1, seventh line under OTHER PUBLICATIONS (Approx.), delete "amendement" and insert -- amendment --, therefor.

On Title page 2, column 2, line 55 (Approx.), delete "Defendents'" and insert -- Defendants' --, therefor.

On Title page 3, column 2, line 21 (Approx.), delete "Inc's" and insert -- Inc.'s --, therefor.

On Title page 6, second column, line 14 (Approx.), delete "Ideopathic" and insert -- Idiopathic --, therefor.

On sheet 4 of 6 (Fig. 6, above Reference Numeral 96), delete "10a" and insert -- 6a --, therefor.

On sheet 4 of 6 (Fig. 6, below Reference Numeral 100), delete "10a" and insert -- 6a --, therefor.

UNITED STATES PATENT AND TRADEMARK OFFICE
CERTIFICATE OF CORRECTION

PATENT NO. : 7,396,355 B2
APPLICATION NO. : 10/872646
DATED : July 8, 2008
INVENTOR(S) : Goldman et al.

It is certified that error appears in the above-identified patent and that said Letters Patent is hereby corrected as shown below:

At column 9, line 64 (Approx.), delete "in.)." and insert -- in). --, therefor.

At column 17, line 29 (Approx.), delete "vasocontrictive" and insert

-- vasoconstrictive --, therefor.

Signed and Sealed this

Thirtieth Day of September, 2008

JON W. DUDAS
*Director of the United States Patent and Trademark Office*